US005711946A

United States Patent [19]
Chand-Goyal et al.

[11] Patent Number: 5,711,946
[45] Date of Patent: Jan. 27, 1998

[54] CONTROL OF POST-HARVEST FUNGAL DISEASE USING SAPROPHYTIC YEAST

[75] Inventors: Tara Chand-Goyal, Riverside, Calif.; Robert A. Spotts, Hood River, Oreg.

[73] Assignee: The State of Oregon Acting by and through the State Board of Higher Education on behalf of Oregon State University, Corvallis, Oreg.

[21] Appl. No.: 392,551

[22] Filed: Feb. 17, 1995

[51] Int. Cl.⁶ .......................... A01N 63/00; A01N 63/04; A01N 25/00; C12N 1/16
[52] U.S. Cl. .................... 424/93.51; 424/405; 435/255.1
[58] Field of Search ................................ 424/93.51, 405; 435/255.1

[56] References Cited

U.S. PATENT DOCUMENTS

| | | | |
|---|---|---|---|
| 5,041,384 | 8/1991 | Wilson et al. | 435/255 |
| 5,238,690 | 8/1993 | Elad et al. | 424/93 Q |
| 5,244,680 | 9/1993 | Roberts | 424/93 S |
| 5,266,316 | 11/1993 | Elad et al. | 424/93 Q |
| 5,270,059 | 12/1993 | Janisiwicz et al. | 424/935 |
| 5,314,691 | 5/1994 | Coffey et al. | 424/93 Q |

FOREIGN PATENT DOCUMENTS

| | | |
|---|---|---|
| PCTUS90/04290 | 7/1990 | WIPO. |
| WO91/01641 | 2/1991 | WIPO. |
| PCTAU92/00157 | 4/1992 | WIPO. |
| WO92/18009 | 10/1992 | WIPO. |

OTHER PUBLICATIONS

Chalutz et al., "Postharvest Biocontrol of Green and Blue Mold and Sour Rot of Citrus Fruit by *Debaryomyces hansenii*," *Plant Disease*, 74:134–137 (1990).

Martini et al., "A New Approach to the Study of Yeast Ecology of Natural Substrates," *Can. J. Microbiol.*, 26:856–859 (1980).

Guerzoni et al., "Analysis of Yeast Flora Associated with Grape Sour Rot and of the Chemical Disease Markers," *Appl. Environ. Microbiol.*, 53:571–576 (1987).

Wisniewski et al., "Biological Control of Postharvest Diseases of Fruits and Vegetables: Recent Advances," *HortScience*, 27:94–98 (1992).

Spurr, "The Microbiol Ecology of Fruit and Vegetable Surfaces: Its Relationship to Postharvest Biocontrol," in Wilson and Wisniewski (ed.), *Biological Control of Postharvest Diseases: Theory and Practice*, CRC Press, Boca Raton, FL, pp. 11–23 (1994).

Wilson et al., "Potential of Induced Resistance to Control Postharvest Diseases of Fruits and Vegetables," *Plant Dis.*, 78:837–844 (1994).

*Primary Examiner*—David M. Naff
*Assistant Examiner*—Deborah K. Ware
*Attorney, Agent, or Firm*—Klarquist, Sparkman Campbell Leigh & Whinston, LLP

[57] ABSTRACT

The present invention provides compositions and methods for biological control of fungal diseases of agricultural commodities such as pome fruits, particularly saprophytic yeasts. Against a number of fungal pathogens, microbial biological control agents, such as the yeast strains of the present invention, show surprisingly effectiveness when used in combination with low levels of chemical fungicides. The present invention also provides methods for isolating microbes useful in controlling fungal diseases of agricultural commodities.

23 Claims, 3 Drawing Sheets

CONTROL OF POST-HARVEST FUNGAL DISEASE USING SAPROPHYTIC YEAST

DESCRIPTION

1. Technical Field

This invention is related to the field of biological control by saprophytic yeast of fungal diseases of agricultural commodities.

2. Background Art

Postharvest spoilage of agricultural commodities such as fruits and vegetables has been estimated to result in losses of approximately 24% of the crop in the United States and up to 50% of the crop worldwide. Preharvest losses of agricultural commodities are also significant.

Much of the pre- and postharvest loss is due to fungal diseases, such as molds and rots. Often infection is initiated by injuries made at harvest or by mechanical wounds to the surface of the agricultural commodity during processing. Chemical fungicides are the principal means of controlling postharvest losses due to fungal disease. The traditional method of fungicide use is to treat fruit after harvest and before storage with chemical fungicides. However, fungicide-tolerant strains are present in most packing houses, rendering chemical fungicides less effective or totally ineffective. For this reason, multiple fungicides are sometimes used simultaneously to improve control of fungal pathogen. There are several important fungal pathogens, e.g., Mucor spp., for which there is currently no effective postharvest fungicide.

An additional problem with the use of chemical fungicides is the fact that many are carcinogenic or environmentally hazardous. At a time when synthetic pesticide use is being curtailed, there is clearly an urgent need to develop safe, new and effective methods of controlling postharvest diseases of agricultural commodities that are safe, environmentally benign, and effective.

There have been numerous reports of attempts to control fungal diseases of agricultural commodities using microbial biological control agents, as reviewed in Wisniewski and Wilson, HortScience, 27:94–98, 1992. Ideally, such biological control agents are naturally occurring saprophytic microorganisms which do not produce antifungal compounds, do not grow at human body temperature, and are consistent in controlling the target disease. Patents and patent applications describing attempts to use bacteria and yeasts for biological control of fungal disease of agricultural commodities include U.S. Pat. Nos. 5,314,691 (Coffey et al.), 5,270,059 (Janisiwicz et al.), 5,266,316 (Elad et al.), 5,244,680 (Roberts), 5,238,690 (Elad et al.), and 5,041,384 (Wilson and Chalutz), and WO 92/18009 (Shanmuganathan) and WO 91/01641 (Wilson et al.). However, despite a significant amount of research, there is no commercially available biological control agent that has proved consistently effective in controlling fungal disease of agricultural commodities. See, e.g., Wisniewski and Wilson, HortScience, 27:94–98, 1992, and Wilson et al., Plant Dis. 78:837–844, 1994.

Most researchers have used a "silver bullet" approach in the selection of microbial biological control agents, identifying a single microbe for biological control of fungal disease rather than documenting the diverse microflora on fruit or vegetable surfaces grown in different locations, then testing the efficacy of these microbial colonists in controlling postharvest diseases (Spurr, "The microbial ecology of fruit and vegetable surfaces: Its relationship to postharvest biocontrol," in: Wilson and Wisniewski (eds.), Biological Control of Postharvest Diseases: Theory and Practices, CRC Press, Boca Raton, Fla., pp. 11–23, 1994). There is a need for an efficient method for the recovery of diverse microflora, saprophytic yeast or bacterial colonists that effectively control postharvest diseases of fruits, including microbes that have a very low population on the plant surface.

SUMMARY OF THE INVENTION

The present invention provides yeast strains that are highly effective in reducing the incidence and/or severity of fungal disease of agricultural commodities, such as fruit, caused by a number of important fungal pathogens.

Accordingly, it is an object of the invention to provide compositions for biological control of a fungal disease of an agricultural commodity comprising an effective amount of one or more biologically pure yeast strains selected from the group consisting of *Cryptococcus infirmo-miniatus* (preferably *Cryptococcus infirmo-miniatus* Phaff and Fell isolate YY-6), *Cryptococcus albidus* isolate HRB-2, *Cryptococcus laurentii* (Kufferath) Skinner isolate HRA-5, *Rhodotorula aurantiaca* isolate YCL-5, *Rhodotorula glutinis* Harrison isolate HRA-3, *Rhodotorula glutinis* Harrison isolate HRA-4, and *Rhodotorula glutinis* Harrison isolate HRB-6. Such compositions provide surprisingly effective biological control of fungal disease caused by a variety of important fungal pathogens of agricultural commodities such as fruit (e.g., pear, apple, or cherries). These fungal pathogens include but are not limited to *Penicillium spp.*, *Botrytis spp.*, *Mucor spp.*, *Pezicula spp.*, and *Phialophora spp.*, and *Monilinea spp.*

It is also an object of the invention to provide methods for controlling a fungal disease of an agricultural commodity comprising applying to the agricultural commodity an effective amount of such a composition.

The present invention also encompasses a method of controlling the incidence or severity of disease caused by a *Phialophora spp.* comprising applying to an agricultural commodity an effective amount of a composition comprising a biologically pure strain of *Rhodotorula spp.* or *Cryptococcus infirmo-miniatus*.

It has also been discovered that a combination of a microbial biological control agent, including the yeast strains listed above, in combination with low levels of a chemical fungicide is surprisingly synergistic in controlling the incidence and severity of a variety of fungal diseases. An effective amount of such a combination may comprise an amount of the chemical fungicide about 25% or less of the normal amount of the fungicide, i.e., an amount that would be effective if the chemical fungicide were to be applied without the microbial biological control agent, preferably about 10% or less of the normal amount, more preferably about 5% or less, and most preferably about 3% or less of the chemical fungicide.

It is a further object of the invention to provide novel methods for isolating from agricultural commodities a highly diverse population of microbes, e.g., bacteria, yeast, and filamentous fungi, that are useful for the biological control of fungal disease. Such methods comprise the steps of: providing an undamaged whole agricultural commodity, such as a fruit, that has preferably not been treated with a biocide (e.g., pesticide, fungicide, etc.); submersing the agricultural commodity in a nutrient-poor aqueous solution; sonicating the submersed agricultural commodity for about one to five minutes (preferably for about five minutes), thereby producing a sonicate; plating the sonicate on a nutrient-poor media under conditions appropriate for growth of the microbe; identifying the microbe; and testing the microbe for efficacy in controlling the incidence and/or severity of fungal disease. Preferably the sonication step is combined of follows a step of shaking the submersed agricultural commodity, e.g., for about one to five minutes. In this way one may isolate, for example, strains of *Cryptococcus infirmo-miniatus, Cryptococcus albidus, Cryptococcus laurentii, Rhodotorula aurantiaca*, and *Rhodotorula glutinis* in addition to those described below.

MODES FOR CARRYING OUT THE INVENTION

Figure 1A:
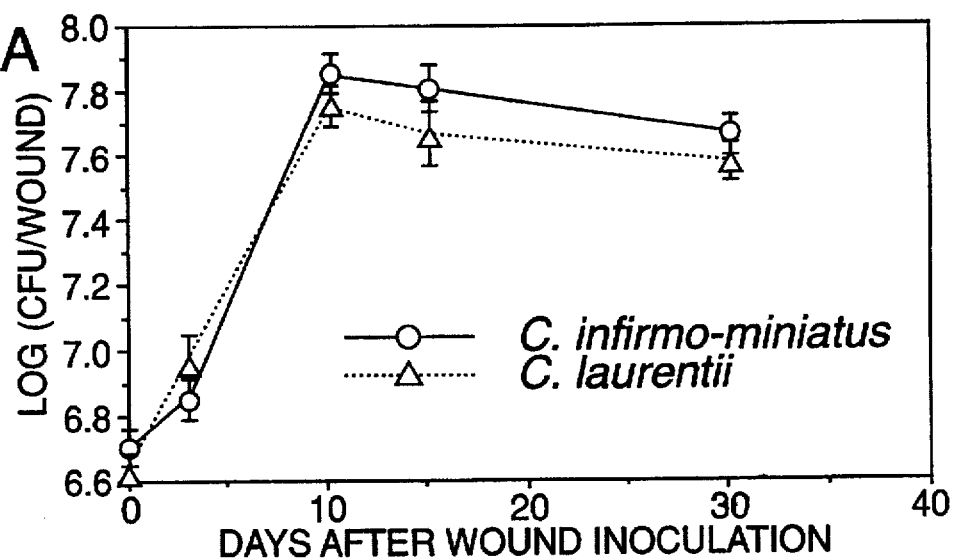
FIG. 1 shows the growth and population dynamics of *Cryptococcus infirmo-miniatus* and *Cryptococcus laurentii* in wounds of Golden Delicious apple fruits stored at (A) 0° C., (B) 5° C., (C) 10° C., and (D) 20° C. Bars represent the standard deviation.

Biocontrol of Fungus Infections of Agricultural Commodities with Saprophytic Yeast Applied Alone or in Combination With A Chemical Fungicide For biological control of fungal pathogens of agricultural commodities, i.e., reducing the incidence and/or severity of disease caused by such fungal pathogens, *Cryptococcus albidus* (preferably strain HRB-2), *Cryptococcus infirmo-miniatus* strain YY-6, *Cryptococcus laurentii* (preferably strain HRA-5), *Rhodotorula aurantiaca* (preferably strain YCL-5), and *Rhodotorula glutinis* (preferably strains HRA-3, HRA-4 and HRB-6) are preferred. These yeast strains are effective against a wide variety of fungal pathogens of agricultural commodities.

It has been discovered that a wide variety of microbial biological control agents are surprisingly synergistic in controlling fungal pathogens of agricultural commodities when used together with low doses of well known chemical fungicides. Although the discussion below focuses on the use of strains of Cryptococcus and Rhodotorula either alone or in combination with a chemical fungicide, this discovery extends to combinations of low doses of chemical fungicides with any microbial biological control agent effective against fungal pathogens of agricultural commodities.

This discovery has important practical implications. Natural populations of fungal pathogens of agricultural commodities commonly comprise a mix of sensitive and insensitive strains. The spores of sensitive strains will not germinate or growth will be slowed by a chemical fungicide. Thus, the inoculum dose of the pathogen will be lowered and the yeast will compete more effectively. With fungicide-insensitive pathogens, even the high rate of fungicide will not be effective, but the yeast in the combination will give effective biological control.

The present invention provides "biologically pure" strains of microbial biological control agents, including saprophytic yeasts such as *Cryptococcus spp.* and *Rhodotorula spp*, and compositions comprising such biologically pure strains. A biologically pure strain of a microbe is one isolated from its natural environment (e.g., the surface of a fruit) and which is not contaminated by other microbial strains. Preferably, the biologically pure strain originates from a single cell of the microbe and thus represents a clonal population.

Biological Control of *Penicillium spp.*

At least 11 species of Penicillium have been isolated from pome fruits naturally infected with blue mold, but *Penicillium expansum* is the most common and economically important species. Blue mold, also known as soft rot and wet rot, is the most important postharvest disease of apples and is also important on other fruits, including pears, for example.

The present invention provides strains of naturally occurring saprophytic yeast effective in reducing the incidence and severity of fungal disease of agricultural commodities caused by *Penicillium spp.*, including but not limited to *Penicillium expansum*. For reducing the incidence and severity of disease caused by *Penicillium spp., Cryptococcus infirmo-miniatus* (preferably strain YY-6), *Cryptococcus laurentii* (preferably strain HRA-5), *Rhodotorula aurantiaca* (preferably strain YCL-5), and *Rhodotorula glutinis* (preferably strains HRA-4 and HRB-6) are preferred, particularly for control of blue mold. Most preferred are *Cryptococcus infirmo-miniatus* isolate YY-6, *Cryptococcus laurentii* strain HRA-5, and *Rhodotorula glutinis* strain HRB-6.

Disease caused by Penicillium may be treated by application of one or more of these yeasts alone or in combination with a low dose of an appropriate chemical fungicide, as defined below. For example, for control of blue mold, about 3% of the normal dose of thiabendazole may be used in combination with *Cryptococcus laurentii* strain HRA-5, *Rhodotorula aurantiaca* strain YCL-5, and *Rhodotorula glutinis* strain HRB-6 as described in greater detail below.

Biological Control of *Mucor spp.*

The present invention provides strains of naturally occurring saprophytic yeast effective in reducing the incidence and severity of fungal disease of agricultural commodities caused by *Mucor spp.*, including but not limited to *Mucor piriformis*. Mucor rot, which is caused primarily by *Mucor piriformis* E. Fischer, occurs less consistently than blue mold and gray mold, although in special situations it can cause severe losses of apples and pears. All fungicides currently registered for postharvest treatment of pome fruits are ineffective against *Mucor piriformis*.

For reducing the incidence and severity of diseases of agricultural commodities caused by *Mucor spp., Cryptococcus infirmo-miniatus* (preferably strain YY-6), *Cryptococcus laurentii* (preferably strain HRA-5), and *Rhodotorula glutinis* (preferably strain HRB-6) are preferred, particularly for control of Mucor rot. Most preferred is *Cryptococcus infirmo-miniatus* isolate YY-6.

Biocontrol of *Botrytis spp.*

The present invention provides strains of naturally occurring saprophytic yeast effective in reducing the incidence and severity of fungal disease of agricultural commodities caused by *Botrytis spp.*, including but not limited to gray mold, caused by *Botrytis cinerea* Pers. Gray mold is the most important postharvest disease of pears and is second to blue mold in importance on apples. Also known as cluster rot or nest rot, gray mold can cause large losses because of its ability to spread from infected to adjacent healthy fruit during storage. The disease develops more rapidly during cold storage temperature than any other postharvest decay except Mucor rot.

For reducing the incidence and severity of diseases of agricultural commodities caused by *Botrytis spp.*, *Cryptococcus infirmo-miniatus* (preferably strain YY-6), *Cryptococcus laurentii* (preferably strain HRA-5), and *Rhodotorula glutinis* (preferably strain HRB-6) are preferred, particularly for control of gray mold. It is preferred that the treatment combine one or more strains of the yeasts of the invention with a low dose of a chemical fungicide known in the art to be effective against *Botrytis spp.*, e.g., thiabendazole, thiram, or dichloran.

Biocontrol of *Phialophora spp.*

The present invention provides strains of naturally occurring saprophytic yeast effective in reducing the incidence and severity of fungal disease of agricultural commodities caused by *Phialophora spp.*, including but not limited to *Phialophora malorum*, which causes side rot. Benzimidazole fungicides such as thiabendazole are ineffective in reducing the incidence and severity of side rot.

For reducing the incidence and severity of diseases of agricultural commodities caused by *Phialophora spp.*, *Cryptococcus infirmo-miniatus* (preferably strain YY-6), *Cryptococcus laurentii* (preferably strain HRA-5), and *Rhodotorula glutinis* (preferably strain HRB-6) are preferred, particularly for control of side rot. The treatment may employ one or more strains of the yeasts of the invention alone or in combination with a low dose of a chemical fungicide.

Biocontrol of *Pezicula spp.*

The present invention provides strains of naturally occurring saprophytic yeast effective in reducing the incidence and severity of fungal disease of agricultural commodities caused by *Pezicula spp.*, including but not limited to *Pezicula malicorticis*, which causes bull's-eye rot.

For reducing the incidence and severity of diseases of agricultural commodities caused by *Pezicula spp.*, *Cryptococcus infirmo-miniatus* (preferably strain YY-6), *Cryptococcus laurentii* (preferably strain HRA-5), and *Rhodotorula glutinis* (preferably strain HRB-6) are preferred, particularly for control of bull's-eye rot. The treatment may employ one or more strains of the yeasts of the invention alone or in combination with a low dose of a chemical fungicide.

Biocontrol of *Monilinea spp.*

The present invention provides strains of naturally occurring saprophytic yeast effective in reducing the incidence and severity of fungal disease of agricultural commodities caused by *Monilinea spp.*, including but not limited to *Monilinea fructicola*, which causes brown rot of cherries.

For reducing the incidence and severity of diseases of agricultural commodities caused by *Monilinea spp.*, *Cryptococcus laurentii* (preferably strain HRA-5) is preferred, if used alone, or, in combination with a chemical fungicide, such as iprodione, *Cryptococcus laurentii* (preferably strain HRA-5) or *Cryptococcus infirmo-miniatus* (preferably strain YY-6) are preferred, particularly for control of brown rot. The treatment may employ one or more strains of the yeasts of the invention alone or in combination with a low dose of a chemical fungicide.

Preparation and Application of the Yeasts of the Invention for Biological Control of Fungal Disease of Agricultural Commodities Growth of Yeast.

The yeast strains of the present invention are grown under aerobic conditions at any temperature satisfactory for growth of the organism, e.g., from about 10° C. to about 30° C. The preferred temperature is 20°–25° C. The pH of the nutrient medium is preferably about neutral; i.e., approximately pH 5.8 to 7.2. The incubation time is that time necessary for the organisms to reach a stationary phase of growth. Incubation time is preferably from about 48–72 hours.

The yeast strains may be grown by any of the methods known in the art for such yeast. For small scale fermentation, conventional shaker flasks are preferred. For large scale fermentation, fermentation tanks are preferred. Agitation and/or aeration is preferably supplied to the inoculated liquid medium. Following incubation, the organisms are harvested by conventional methods, e.g., centrifugation or filtering. Cultures or harvested cells may be stored by conventional means, e.g., by freeze drying after addition of a cryoprotectant.

Amount of yeast in the compositions of the invention.

The compositions of this invention are generally provided in an amount effective to treat and/or prevent fungal disease of agricultural commodities. An "effective amount" of a composition of the present invention is an amount of the composition which reduces the incidence or severity of a fungal disease when applied to the agricultural commodity, preferably by 50% or more as compared with controls.

As will be apparent to one skilled in the art, effective concentrations may vary depending upon factors including: the strain of yeast employed, the type, age, and ripeness of agricultural commodity; and the type and concentration of fungal pathogens affecting the agricultural commodity; temperature and humidity. Exemplary concentrations range from about $1 \times 10^4$ to $1 \times 10^{12}$ colony forming units per milliliter (CFU/ml). Preferably, compositions comprise in excess of $1 \times 10^7$ CFU/ml.

Modes of Application of the Compositions of the Present Invention.

The compositions of the present invention may be provided in any of the standard forms known in the art. These fungal biocontrol compositions may be in a solid or liquid form. Solid compositions may be in the form of lyophilized yeast in the form of dusts, granules, or wettable powders. Lyophilized cultures may be readily re-suspended in aqueous solutions for application to agricultural commodities. Liquid compositions may be in the form of aqueous or non-aqueous media, in solutions, suspensions, dispersions, dispensions, or concentrated form, e.g., a slurry or paste.

Compositions comprising yeast of the present invention may be applied by any method known in the art, including but not limited to spraying, dipping, drenching, brushing, or misting. In addition, the organisms of the invention may be incorporated into waxes, wraps or other protective coatings used in processing the agricultural commodities.

Fungal Pathogens.

The yeasts of the present invention are useful for the biological control of the incidence and severity of pre- and postharvest disease caused by a variety of plant pathogens, including those which cause disease in pome fruits such as pear and apple. Examples of plant pathogens against which the yeast of the invention are useful include, but are not limited to, *Penicillium spp.* (e.g., *Penicillium expansum*), *Botrytis spp.* (e.g., *Botrytis cinerea*), *Mucor spp.* (e.g., *Mucor piriformis*), *Pezicula spp.* (e.g., *Pezicula malicorticis*), *Phialophora spp.* (e.g., *Phialophora malorum*), and *Monilinea spp.*, e.g., *Monilinea fructicola*.

These fungi affect a wide variety of agricultural commodities. For a listing of fungal plant pathogens and their distribution and host range see, e.g., Farr et al., eds., Fungi on Plants and Plant Products in the United States, American Phytopathological Society, St. Paul, Minn., 1989 (No. 5 in the series Contributions from the U.S. National Fungus Collections).

Agricultural Commodities.

The yeasts of the present invention are useful in controlling plant pathogens on a variety agricultural commodities including, but not limited to: fruits, vegetables, cereals, grains (e.g., wheat, corn, sorghum, soybean, and barley), nuts (e.g., peanuts, almonds, and pecans), seeds, floral bulbs, nursery seedlings, and silage. Examples of fruits include but are not limited to: pome fruits (e.g., apples and pears), stone fruits (e.g., peaches, nectarines, apricots, plums, and cherries), citrus fruits (e.g., grapefruit, orange, lemon, kumquat, lime, mandarines and pummelo), grapes, tomatoes, persimmons, strawberries, and papayas. Apples which may be treated in accordance with this invention include Granny Smith, Red and Golden Delicious, Jonathan, Gala, Fuji, Newton, Macintosh, and other well known apple strains. Examples of pears include d'Anjou, Packham's Triumph, William's Bon Chretian, and Beurre Bosc. In addition to unprocessed agricultural commodities, the present invention may be utilized with processed agricultural commodities including, for example, raisins, prunes, figs, dried apricots, and dates.

Fruit treated in accordance with the methods of this invention may be stored at standard fruit storage temperatures, such as 0° C., 4° C., and room temperature, free of the effects of fungal infection or with reduced incidence and/or severity of infection. Fruit treated in accordance with this invention may also be stored in a controlled atmosphere (such as 2.5% oxygen and 2.5% carbon dioxide).

The agricultural commodity may be treated at any time before or after harvest. The preferred time of treatment is after harvest and prior to storage or shipment.

Fungicides.

The microbial biological control agents of the present invention, such as the saprophytic yeast strains disclosed herein, may be used to control the incidence and severity of fungal disease in agricultural commodities in combination with one or more well known chemical fungicides, including but not limited to: benzamidazoles (including benomyl, carbendazim, and thiabendazole), thiram, dichloran, vinclozolin, iprodione, procymidon, dichlorfluanide, tebuconazole, prochloraz, fenethanil, diethefencarb, metomeclan, chlorothalonil, and mixtures of these fungicides.

If a microbial biological control agent is applied in combination with a chemical fungicide used in combination, it is preferred that "low levels" of the chemical fungicide be used. A "low dose" of a chemical fungicide is defined as about 25% or less of the amount or dosage of the chemical fungicide commonly used for control of a particular fungal disease when applied alone, more preferably about 10% or less, even more preferably about 5% or less, and most preferably about 3% or less.

The chemical fungicide may be applied in a composition comprising the yeast and the chemical fungicide or the chemical fungicide may separately applied, either before or after the application of the yeast, using any well known method of application, including but not limited to spraying, dipping, drenching, misting, and incorporation into packaging materials. Benzimidazole and dicarboximide fungicides, for example, are commonly applied as postharvest dips, drenches or line sprays.

Combination of the Yeasts of the Invention with each Other and with Other Biological Control Agents.

The yeast strains of the present invention may be used individually or in combination with one or more other yeast strains of the invention. The yeast strains of the present invention may also be used in combination with other microbes used for the biological control of fungal or other diseases of agricultural commodities in an amount compatible with the effectiveness of a yeast strain of the present invention. The yeast strains of the present invention and the additional biological control agent may be applied to the agricultural commodity at the same time as part of a single composition or at different times, either before or after application of a yeast of the present invention.

Such additional biological control agents include, but not limited to: *Acremonium breve, Bacillus subtilis, Candida parapsilosis, Candida guilliermondii (Pichia guilliermondii), Cryptococcus albidus, Cryptococcus flavus, Cryptococcus laurentii, Debaryomyces hansenii, Enterobacter aerogenes, Hanseniaspora uvarum, Myrothecium roridum, Pseudomonas cepacia, Pseudomonas syringae, Pseudomonas gladioli, Rhodotorula glutinis, Rhodotorula mucilaginosa, Sporobolomyces roseus, Trichoderma harzianum*, and *Trichoderma pseudokoningii*.

Derivatives and Mutants.

This invention extends to derivatives and mutants of the yeast strains of the invention which are likewise effective in the biological control of fungal disease of agricultural commodities. Such derivatives or mutants may be prepared according to standard microbiological or recombinant DNA methods, such as mutagenesis with chemical mutagens (e.g., nitrosoguanidine and ethanemethylsulphonate), or irradiation (e.g., ultraviolet radiation, infrared radiation, and irradiation with X-rays or gamma rays or a source emitting alpha or beta particles), spontaneous mutation, mutagenesis using recombinant DNA techniques, and transformation with heterologous nucleic acids, including recombinant plasmid or viral vectors. Derivatives or mutants may differ from the parent strains in respect of one or more morphological, biochemical, physiological, or other characteristics, but will retain the capacity to inhibit growth of fungal pathogens.

Carriers, Excipients, and Other Additives.

The yeast strains of the present invention may be present in compositions comprising one or more agriculturally acceptable carriers, excipients, or other materials as are known in the art, agriculturally compatible, and compatible with the viability, growth, and effectiveness of the yeast strains of the present invention in biological control of fungal pathogens.

The term "carriers" includes, for example, (1) a gel or gum based carrier (e.g., xanthan gum) or (2) a water based carrier (e.g., water, buffer solutions, carbohydrate containing solutions, and saline solutions); (3) an oil based carrier (e.g., "Fresh Mark" or "Fresh Wax 58P" (which is a paste wax for peaches, plums and nectarines, containing—white oil, paraffin wax, petrolatum and oleic acid) both from Fresh Mark (Chemical Corporation, Orlando, Fla.); (4) a wax based carrier (e.g., including wax coatings typically used on citrus fruit and apples, for example "Britex 551" or "Britex 559," both from Broshar (Chemicals) Ltd., Kefar-Saba, Israel); (5) a powdered carrier ingredient to provide the composition in powdered form, and in which the microorganism(s) are dispersed and thus diluted to a desired concentration in the powdered composition (e.g., starch and talc); and (6) a mixture of the foregoing.

The term "excipient" refers to conventional additives, such as surfactants and wetting agents (e.g., Tween 20 and Triton X-100), antioxidants, nutrients, emulsifiers, spreading agents, suspending agents, sticking agents, anti-scald agents (e.g., diphenylamine or ethoxyquin), preservatives, chemical pesticides and the like. The compositions of the invention may also comprise a source of calcium, such as calcium chloride or other non-toxic calcium source in an amount from 0.1 to 50% (v/v). See WO 92/18009 (Shanmuganathan). Preservatives may include, for example: (a) a gum, e.g., a natural gum, such as guar gum, locust bean gum, karaya gum, tragacanth gum or preferably xanthan gum; (b) methyl cellulose; (c) silica gel; and (d) mixtures of the foregoing.

Isolation of Saprophytic Yeast Strains Effective in Fungal Biocontrol

The present invention provides methods for isolating diverse microflora and accurately estimating the population size and diversity of culturable yeasts and bacteria on the surface of fruit at harvest and in cold storage. Moreover, these methods are useful for obtaining microorganisms on the surface of fruit that are effective in the biocontrol of fungal pathogens, such as those responsible for postharvest losses of fruit.

Plant surfaces are colonized by diverse microbial flora. At harvest, the microbial community on the fruit surface includes bacteria, fungi, yeasts, and other microorganisms (Andrews and Kenerley, Can. J. Microbiol. 24:1058–1072, 1978; Andrews and Kenerley, Can. J. Microbiol. 25:1331–1344, 1979; Spurr, 1994). Some microorganisms casually occupy plant surfaces and are unable to multiply (Hirano and Upper, Annu. Rev. Phytopathol. 21:243–269, 1983). These microorganisms soon disappear unless replenished. Other microorganisms are epiphytic residents able to grow and survive on plant surfaces.

This microbial population plays an important role in the development of postharvest rots of fruits and vegetables (Chalutz and Wilson, Plant Dis. 74:134–137, 1990; Spurr, 1994). Disease incidence has been positively correlated to the size of the epiphytic population of plant pathogenic bacteria (Rouse et al., Phytopathol 75:505–509, 1985).

Yeasts colonize plant surfaces or wounds for a long period under dry conditions, produce extracellular polysaccharides that enhance their survivability, rapidly multiply and use available nutrient, and are impacted minimally by pesticides (Wisniewski and Wilson, HortScience 27:94–98, 1992).

A number of methods have been described for removing saprophytic microorganisms from plant surfaces. Swabbing has been reported to be less efficient than pulping for removal of yeasts from apple fruit surfaces (Marshall and Walkey, Food Res. 16:448–456, 1951) and is also less efficient than shaking or sonication for removal of fungal conidia from the surface of grape or plum fruits. Swabbing introduces the additional problem of removing organisms from the swabs (Walters, J. Appl. Bacteriol. 30: 56–65, 1967). Other methods for removal of microorganisms include: washing samples in water (Le Roux et al., Phytophylactica 5:51–54, 1973; El-Din et al., Zentralbl. Mikrobiol. 141:488–492, 1986; Kamra and Madan, Microbios. Letters 34:79–85, 1987; Roberts, Phytopathol. 80: 526–530, 1990), water-Tween (Guerzoni and Marchetti, Appl. Environ. Microbiol. 53: 571–576, 1987) or phosphate buffer (Janisiewicz, Phytopathol. 77:481–485, 1987).

This washing step is normally followed by vortexing or shaking the suspension, then plating the suspension on agar media. Blending of strawberries (Buhagiar and Barnett, J. Appl. Bact. 34:727–739, 1971) and grapes (Singh and Kainsa, Indian Phytopathol. 36:72–76, 1981) in phosphate buffer has been used to study the microflora of fruit. Ultrasound has also been employed to facilitate harvesting and quantification of plant epiphytic microorganism (Martini et al., Can. J. Microbiol. 26:856–859, 1980; Guerzoni and Marchetti, Appl. Environ. Microbiol. 53: 571–576, 1987). It has been reported that ultrasonication resulted in dislodgement of higher numbers of yeasts species from plant surface and consistently resulted in 100–200 percent more yeast species than other methods (Martini et al., Can. J. Microbiol. 26:856–859, 1980). However, none of these reports document the optimum time of sonication that is necessary for the detachment of most microorganisms from plant surfaces and for isolation of the most diverse microbial flora.

For standard procedures for isolation and cultivation of yeast strains, see also Phaff, Miller and Mrak, The Life of Yeasts, 2nd edition, Harvard University Press, 1978; and Devenport, Outline Guide to Media and Methods for Studying Yeasts and Yeast-like Organisms, in Biology and Activity of Yeasts, A.P. London, 1980. Yeast strains may be grown on nutrient agar (e.g., potato dextrose agar). Yeast strains can be readily typed according to standard procedures, such as are described in Barnet et al., Yeasts: Characteristics and Identification, Cambridge University Press, 1983.

The methods of the present invention optimize the recovery of a diverse microbial population, particularly those useful for fungal biocontrol, from fruit or other agricultural commodities.

Briefly stated, a healthy, mature agricultural commodity, e.g., a fruit, preferably free from punctures or other types of damage and preferably not treated with a bactericide, fungicide or insecticide, is randomly selected. Fruit that has not been treated for pest control, such as from a neglected orchard, is preferred in order to ensure a more diverse microbial population.

If the fruit must be stored prior to microbial isolation, storage at a low temperature, e.g., at approximately 5° C., is preferred in order to preserve natural microbial populations; storage at a higher temperature is expected to favor bacteria and adversely affect yeasts. It is preferred that the fruit be stored for 24 hours or less.

The fruit, along with its stem, is partially or fully submersed in an aqueous buffer, e.g., SPBT (0.005M sterile potassium phosphate buffer, pH 7.0, 0.005% Tween 80). A low-nutrient medium simulates the low nutrient status of fruit surfaces, whereas high nutrient media may cause fast-growing yeasts or bacteria to overgrow the plates or actually prove toxic to some yeasts.

Microbes on the surface of the fruit are dislodged, by shaking, followed by sonication, preferably for one to five minutes, most preferably for five minutes. It has been determined that this combination treatment is highly effective in detaching tightly bound microbes and optimizes the recovery of a diverse population of bacteria, yeast, and filamentous fungi.

Culturable populations of yeasts, bacteria and filamentous fungi are plated on an appropriate media, preferably a nutrient-poor media, under conditions appropriate for growth of the microbe. The plates are carefully examined by visual inspection for differences in the morphological and biochemical characteristics of the colonies in order to identify and select the most diverse microbial populations.

Nutrient-poor media are preferred for plating the microbes, e.g., diluted YM agar and diluted nutrient broth agar for the isolation of yeasts and bacteria, respectively. Colony characteristics are more stable and better defined on nutrient-poor agar media than on nutrient-rich media. Often, different strains or species will have subtle differences in colony morphology which can be observed on nutrient-deficient media, but not on nutrient-rich media. Moreover, fast-growing colonies of a few yeasts or bacteria are less likely to overgrow nutrient-poor media plates and prevent the development of slower-growing isolates. Pigmentation and macro- and micro-morphological characteristics of yeast and bacterial colonies have been found to be stable as long as the composition of the agar medium and the incubation temperature are not changed.

In order to isolate diverse bacterial populations, the media is preferably supplemented with agents that prevent fungal growth without interfering with bacterial growth, e.g., cyclohexamide; for the isolation of yeasts and filamentous fungi, the media is supplemented with an agent that restricts radial growth of filamentous fungi without affecting spore germination, e.g., dichloran.

In addition to the method of recovery, factors such as temperature, rainfall, fruit maturity, and regional and local geography have been reported to influence epiphytic microbial population of plants. Therefore, epiphytic yeast and bacterial population size on fruits from different locations of the Pacific Northwest are different.

This simplified recovery method provides a powerful means to isolate naturally occurring bacteria, yeast, and filamentous fungi that are effective biological control agents. This method can also be used to study the population dynamics of yeasts and/or bacteria associated with the surface of an agricultural commodity such as pear or apple fruits.

The invention will be better understood by reference to the following examples, which are intended to merely illustrate the best mode now known for practicing the invention. The scope of the invention is not to be considered limited thereto, however.

EXAMPLES

Example 1

Improved Method for Obtaining Microbes Colonizing the Surface of Fruit and for Studying their Microbial Ecology Healthy mature Golden Delicious apple fruits (*Malus domestica* Borkh.), free from punctures or other types of damage, were randomly selected from an unsprayed orchard. Twenty fruits were collected in each polythene bag. Three bags, each representing a replicate, were placed on ice during transit from the field to the laboratory. The samples were kept in an incubator at 5° C. and processed within a day of sampling and after 4 and 8 weeks of storage.

To determine population size and microbial diversity in associated yeasts, bacteria, and filamentous fungi, three apple fruits, one from each bag, were sampled. Each fruit, along with its stem, was submersed in 600 ml beakers containing 200 ml SPBT (0.005M sterile phosphate buffer, pH 7.0, 0.005% Tween 80). The beakers were placed on a rotary shaker (150 rpm) for 5 min., after which the beakers containing the fruits were placed in an ultrasonic bath having an output of 270 watts and frequency of 43 KHz (model Q140, L & H Manufacturing Company, Kearny, N.J.). During sonication, the fruits were gently rotated every 30 sec using a sterile stainless steel spatula. A 5.0 ml sample of buffer was removed from each beaker immediately before sonication and after 1, 2, 5, 10 and 15 min of sonication. The samples were vortexed for 1 min using Vari-Whirlmixer (VWR Scientific, WA) and three sequential 10-fold dilutions were made in SPBT by adding a 0.5 ml of wash buffer to 4.5 ml of SPBT.

Culturable populations of yeasts, bacteria and filamentous fungi were recovered by spreading 0.1 ml of suspension from each replicate onto duplicate plates of agar media. For bacterial populations and diversity, the samples were plated on diluted nutrient broth agar (Chand et al., Appl. Environ. Microbiol. 58:3374–3379, 1992) supplemented with cycloheximide (100 µg/ml) to prevent fungal growth (Hirano et al., Appl. Environ. Microbiol. 44:695–700, 1982). For yeasts and filamentous fungi, the samples were plated on diluted YM agar (DYMA), consisting of 4.1 g of Bacto YM broth (Difco Laboratories, Detroit, Mich.), 18 g Bacto-Agar, 100 mg chloramphemicol and 2 mg dichloran per liter of medium. Dichloran was added to the medium to restrict the radial growth of filamentous fungi without affecting spore germination (Byrde and Willetts, The Brown Rot Fungi of Fruits: Their Biology and Control, Pergamon Press Ltd., Oxford, England, 1977; Pitt and Hocking, Fungi in Food Spoilage, Academic Press, New York, 1985). The inoculated plates were incubated at 20°±1° C. and observed daily. The number of bacterial colony forming units (CFU) per ml of wash buffer was estimated after 14 days of incubation (Chand et al., Appl. Environ. Microbiol. 58:3374–3379, 1992). Yeast and filamemtous fungal CFU per ml of wash buffer were estimated after 7 days of incubation. The surface area of each fruit was measured by peeling its skin with a potato peeler and determining the total surface area ($cm^2$) of skin with an area meter (Li-Cor, model no. LI-3000, Lincoln, Nebr.). The number of CFU $cm^{-2}$ of each fruit was calculated from counts and surface area data.

Colony characteristics (pigmentation, size, opacity, form, elevation, margin, smoothness, texture, and spreading nature) of different types of bacteria have been described (Chand et al., Appl. Environ. Microbiol. 58:3374–3379, 1992; Smibert and Krieg, "General Characterization," p. 409–443 in Gerhardt et al. (eds.), Manual of Methods for General Bacteriology, American Society for Microbiology, Washington, D.C., 1981) and were used to characterize colonies. Pigmentation and macro- and micro-morphological characteristics of yeast colonies were used to characterize diverse yeasts (Guerzone and Marchetti, Appl. Environ. Microbiol. 87:571–576, 1986; Martini et al., Can. J. Microbiol. 26:856–859, 1980; Sasaki and Yoshida, J. Facul. Agr. Hokkaido Univ., Sapporo 51:194–220, 1959). Total counts of filamentous fungi were recorded without characterizing their colonies, because different fungi can have similar colony characteristics.

To isolate the epiphytic yeasts, the fruits were treated as described in the above experiment, except that the volume of SPBT in each beaker was 200 ml and the fruits were sonicated for 5 min. The wash buffer of five fruits, representing a replicate, was combined and plated on DYMA plates, as described above. After 7 days of incubation, yeast colonies having diverse colony characteristics were characterized and enumerated. Yeast colonies having similar and/or different colony characteristics were lifted and streaked on YM agar (Difco Laboratories, Detroit, Mich.) for purification. Purified yeast isolates were stored at −70° to −75° C. (El-Din et al., Zentralbl. Mikrobiol. 141:488–492, 1986).

Using the above described approach, the epiphytic yeast microflora of mature pear fruits from three locations in Oregon (Hood River, Cascade Locks, Medford) and one location in Washington (Yakima) were also studied. There were three replicates, each consisting of five randomly selected fruits from each location per cultivar (Table 4).

The yeasts were identified by Central Bureau for Fungal Culture (CBS), Baarn, the Netherlands, based on morphological characteristics, fermentation of sugars, and growth on different carbon and nitrogen sources.

The yeast strains were identified according to standard procedures.

For *Cryptococcus laurentii* (Kufferath) Skinner isolate HRA-5, fermentation was absent, cells were cream colored, round to oval in shape, and budded on a narrow base. Pseudo hyphae were absent or very simple.

For *Cryptococcus infirmo-miniatus* Pfaff and Fell isolate YY-6, fermentation was absent, cells were pink to red in color, round to oval in shape, and budded on a narrow base. Septate or pseudo hyphae were absent.

For *Rhodotorula glutinis* Harrison isolate HRB-6, fermentation was absent, cells were light pink in color, round to oval in shape, and budded on a narrow base. Septate or pseudo hyphae were absent.

Additional information regarding growth characteristics of isolates HRA-5, YY-6, and HRB-6 are given below:

|  | HRA-5 | YY-6 | HRB-6 |
| --- | --- | --- | --- |
| D-glucose | + | + | + |
| D-galactose | + | + | + |
| L-sorbose | − | + | + |
| D-glucoseamine | + | − | − |
| D-ribose | + | + | + |
| D-xylose | + | + | + |
| L-arabinose | + | + | − |
| L-rhamnose | + | + | + |
| sucrose | + | + | + |
| maltose | + | + | + |
| trehalose | + | + | + |
| methyl-glucoside | + | − | + |
| cellobiose | + | + | + |
| melibiose | + | − | − |
| lactose | + | − | − |
| raffinose | + | + | + |
| melezitose | + | + | + |
| glycerol | − | + | + |
| meso-erythritol | + | − | − |
| D-glucitol | + | + | + |
| D-mannitol | + | + | + |
| myo-inositol | + | + | − |
| 2-keto-D-gluconate | + | + | + |
| D-gluconate | + | + | + |
| D-glucuronate | + | + | − |
| DL-lactate | − | − | + |
| nitrate | − | − | + |
| ethylamine | + | + | + |
| lysine | + | + | + |
| cadaverine | − | − | + |
| growth at 25° C. | + | + | + |
| growth at 30° C. |  |  | + |
| growth at 37° C. | − | − | − |

The lowest population sizes of yeast, bacterial, and filamentous fungi were recovered when samples were not sonicated (Table 1). When the samples were sonicated for 1 min, the recovery of yeasts and bacteria increased substantially. The increase in counts of culturable cells was slower from 1 to 5 min of sonication. Sonication for 10 or 15 min resulted in little increase of recovery of yeast or bacterial CFU cm$^{-2}$ of fruit surface. Recovery of filamentous fungi, however continued to increase even at the longest sonication time. Filamentous fungi adhere to the plant surface more tightly than saprophytic bacteria and yeasts (Nicholson, "Adhesion of fungi to plant cuticle," pp. 74–89 in Roberts and Aist (eds.), Infection Processes in Fungi, Rockefeller Foundation, New York, 1984; Nicholson and Epstein, "Adhesion of fungi to plant surface," pp. 3–23 in Cole and Hoch (eds.), The Fungal Spore and Disease Initiation in Plants and Animals, Plenum, New York, 1991) and more time apparently was required to dislodge them from the fruit surface.

When ultrasonic waves travel through SPBT, they create a scrubbing action that is capable of cleaning up to 16 times more efficiently than hand scrubbing the fruits. Microscopic examination of unsonicated fruit washings revealed the presence of clumps of yeast and bacterial cells. Sonication for 5 min separated these clumps into individual cells. Probably for this reason the numbers of morphologically distinct isolates of yeasts and bacteria did not increase after 5 min of sonication.

In general, the epiphytic yeast population declined during two month storage of fruits at 5° C. (Table 1). The population size of epiphytic bacteria changed very little during storage and no definite pattern of population change was recorded for filamentous fungi.

The lowest and highest number of morphologically distinct colonies of yeasts and bacteria were recovered when samples were not sonicated or sonicated for 5 min, respectively (Table 2). Increase in the sonication time from 5 to 10 or 15 min did not result in any further increase in the diversity of isolates from the fruits.

Diluted YM agar and diluted nutrient broth agar were used for the isolation of yeasts and bacteria, respectively, because colony characteristics have been reported to be more stable and better defined on nutrient-poor agar media than on nutrient-rich media (Chand et al., Appl. Environ. Microbiol. 58:3374–3379, 1992; Hattori, Rep. Inst. Agric. Res. Tohoku Univ., 27:23–30, 1976; Waksman, Principles of Soil Microbiology, The Williams & Wilkins Co., Baltimore, 1932). Occasionally, the buffer wash of the fruits was also plated onto nutrient-rich media (full strength YM agar and nutrient agar for yeasts and bacteria, respectively). In such cases it was observed that the pigmentation and other colony characteristics of yeasts and bacteria were always better defined on nutrient-poor agar-media. Additionally, fast-growing colonies of a few yeasts or bacteria overgrew the nutrient-rich media plates and prevented the development of slow-growing isolates. It was also observed that pigmentation and macro- and micro-morphological characteristics of yeast and bacterial colonies were stable as long as the composition of the agar medium and the incubation temperature were not changed.

The yeast and bacterial population on the surface of unsprayed mature apple fruits at harvest was determined to be approximately 8.0×10$^3$ and 9.5×10$^4$ CFU cm$^{-2}$, respectively.

It was observed that when two yeast isolates showed only minor differences in one of the colony characters such as shade of pigmentation or colony margin, they were identified as the same species; such variability is probably related to strain differences. The isolates that were morphologically distinct from each other were always identified as different species of the same genus or yeasts of different genera. Thus, morphological characteristics may be used to select the most diverse yeast colonists of plant surfaces.

The surface of pear fruit was found to be colonized by at least 31 morphologically different strains of 10 yeast and yeast-like fungal species. This simplified recovery method provides a powerful means to isolate yeasts and bacteria which are effective biocontrol agents, as discussed below. This method can also be used to study the population dynamics of yeasts and/or bacteria associated with the surface of fruit such as pear or apple fruits.

TABLE 1

Effect of sonication on population size of microorganisms recovered from surface of Golden Delicious apple fruits.

| Storage time (weeks) | Sonication time (min)[b] | Colony forming units (×10³)/cm² of fruit surface[a] | | |
|---|---|---|---|---|
| | | Yeast | Bacteria | Filamentous fungi |
| 0 | 0 | 1.4 ± 0.5 | 14.2 ± 3.0 | 0.1 ± 0.0 |
| | 1 | 4.0 ± 1.7 | 49.6 ± 11.9 | 0.3 ± 0.1 |
| | 2 | 4.9 ± 1.3 | 56.7 ± 8.6 | 0.5 ± 0.1 |
| | 5 | 7.7 ± 1.7 | 73.1 ± 8.9 | 0.5 ± 0.1 |
| | 10 | 7.9 ± 1.7 | 91.2 ± 7.6 | 0.8 ± 0.1 |
| | 15 | 8.3 ± 2.1 | 95.4 ± 6.0 | 1.3 ± 0.3 |
| 4 | 0 | 1.9 ± 0.7 | 31.4 ± 6.5 | 1.7 ± 0.9 |
| | 1 | 4.0 ± 0.8 | 60.2 ± 18.6 | 2.3 ± 1.2 |
| | 2 | 4.7 ± 1.0 | 74.5 ± 22.6 | 2.8 ± 1.1 |
| | 5 | 5.4 ± 0.8 | 95.5 ± 37.4 | 3.0 ± 1.1 |
| | 10 | 5.8 ± 1.0 | 99.6 ± 5.3 | 3.8 ± 1.2 |
| | 15 | 6.1 ± 1.3 | 93.3 ± 35.2 | 4.0 ± 1.4 |
| 8 | 0 | 1.1 ± 0.3 | 44.5 ± 19.0 | 1.0 ± 0.4 |
| | 1 | 2.0 ± 0.8 | 71.7 ± 32.0 | 1.1 ± 0.3 |
| | 2 | 2.2 ± 0.9 | 79.2 ± 36.8 | 1.6 ± 0.4 |
| | 5 | 3.5 ± 1.3 | 104.3 ± 52.4 | 1.7 ± 0.4 |
| | 10 | 3.2 ± 1.1 | 115.2 ± 54.8 | 1.6 ± 0.5 |
| | 15 | 3.4 ± 1.4 | 118.6 ± 54.0 | 2.4 ± 0.9 |

[a]Each value is the average of three replications ± standard error.
[b]Each fruit was placed in a beaker (600 ml) containing 200 ml of sterile phosphate buffer tween and placed on to a rotary shaker (150 rpm) before sonication. The wash buffer was plated on diluted YM agar and diluted nutrient broth agar plates for yeasts and bacteria, respectively.

TABLE 2

Effect of sonication and storage on the isolation of morphologically distinct yeast and bacterial isolates from the surface of Golden Delicious apple fruits[a].

| Storage time (weeks) | Sonication time (min) | Number of morphologically distinct isolates | | | | | |
|---|---|---|---|---|---|---|---|
| | | Yeast | | | Bacteria | | |
| | | Min. | Max. | Average | Min. | Max. | Average |
| 0 | 0 | 2 | 3 | 2.3 | 2 | 3 | 2.3 |
| | 1 | 2 | 5 | 3.3 | 2 | 6 | 3.4 |
| | 2 | 3 | 6 | 4.3 | 3 | 7 | 4.3 |
| | 5 | 5 | 7 | 5.7 | 5 | 9 | 6.3 |
| | 10 | 5 | 7 | 5.7 | 5 | 9 | 6.3 |
| | 15 | 5 | 7 | 5.7 | 5 | 9 | 6.7 |
| 4 | 0 | 3 | 4 | 3.3 | 3 | 4 | 3.7 |
| | 1 | 4 | 5 | 4.3 | 4 | 6 | 4.7 |
| | 2 | 4 | 5 | 4.7 | 5 | 7 | 5.7 |
| | 5 | 6 | 8 | 6.7 | 6 | 8 | 6.7 |
| | 10 | 6 | 7 | 6.3 | 6 | 8 | 6.7 |
| | 15 | 6 | 8 | 6.7 | 6 | 8 | 6.7 |
| 8 | 0 | 3 | 4 | 3.7 | 2 | 3 | 2.7 |
| | 1 | 4 | 5 | 4.3 | 4 | 4 | 4.0 |
| | 2 | 4 | 6 | 5.0 | 5 | 5 | 5.0 |
| | 5 | 7 | 8 | 7.3 | 5 | 6 | 5.3 |
| | 10 | 6 | 8 | 6.7 | 5 | 6 | 5.3 |
| | 15 | 7 | 8 | 7.3 | 5 | 6 | 5.3 |

[a]Each fruit was placed in a beaker (600 ml) containing 200 ml of sterile phosphate tween and placed on to a rotary shaker (150 rpm) for 5 min before sonication. The wash buffer was plated on diluted YM agar and diluted nutrient broth agar for yeasts and bacteria, respectively.

TABLE 3

Population size of yeasts isolated from pear cultivars in the Pacific Northwest[a].

| Location | Cultivar | Yeast CFU/cm² of fruit surface | Number of morphologically distinct yeast isolates | | |
|---|---|---|---|---|---|
| | | | Min | Max | Average |
| Hood River | Anjou | 355 ± 33 | 5 | 6 | 5.7 |
| Hood River | Bartlett | 990 ± 233 | 6 | 7 | 6.7 |
| Medford | Bosc | 4115 ± 188 | 3 | 4 | 3.7 |
| Cascade Locks | Bartlett | 6430 ± 616 | 6 | 7 | 6.7 |
| Yakima | Bartlett | 7366 ± 2300 | 6 | 7 | 6.7 |

[a]Fruits (five) of each replicate (three replicates per location) were shaken for 5 min in SPBT and sonicated for five minutes before plating on DYMA medium.

TABLE 4

Yeast colonists of pears in different locations of the Pacific Northwest.

| | Relative abundance (% CFU) of yeasts[a] | | | | |
|---|---|---|---|---|---|
| | Hood River | | Cascade Locks | Medford | Yakima |
| Yeast | Anjou | Bartlett | Bartlett | Bosc | Bartlett |
| Aureobasidium pullulans | 59 (2) | 47 (2) | 39 (1) | 81 (2) | 52 (2) |
| Cryptococcus albidus | — | 37 (1) | 21 (1) | 14 (1) | 25 (2) |
| Cryptococcus infirmo-miniatus | — | 1 (1) | — | — | 1 (1) |
| Cryptococcus laurentii | 13 (1) | 10 (1) | — | — | 19 (1) |
| Debaryomyces hansenii | — | — | 11 (1) | — | — |
| Rhodotorula aurantiaca | — | — | 7 (1) | — | — |
| Rhodotorula fujisanensis | — | — | 14 (1) | — | — |
| Rhodotorula glutinis | 22 (2) | 5 (2) | — | 5 (1) | 3 (1) |
| Rhodotorula minuta | 6 (1) | — | 1 (1) | — | — |
| Sporobolomyces roseus | — | — | 7 (1) | — | — |

[a]Fruits (five) of each replicate (three replicates per location) were shaken for 5 min in SPBT and sonicated for 5 min before plating on to DYMA medium. Value in parenthesis represents the number of morphologically different isolates.

Example 2

Control of Postharvest Pear Disease Using Natural Saprophytic Yeast Colonists and Their Integration with Low Dosage of Thiabendazole Saprophytic yeast colonists of mature pear fruits isolated and identified as described above were tested for their effectiveness in controlling blue mold, gray mold, Mucor rot, bull's-eye rot, and side rot of pear fruit.

Fruits.

Pear fruits, cv. d'Anjou and Bosc, grown at the Mid-Columbia Agricultural Research and Extension Center in Hood River, Oreg., were harvested. At harvest, fruit firmness was 60±2 and 62±2 Newtons and soluble solids were 12.0±2 and 14±1.5, respectively, as determined with a UC pressure test penetrometer (Ametek, Bellingham, Wash.). Soluble solids were measured using a hand refractometer (VWR Scientific, Los Angeles, Calif.).

Fruits were air stored in cardboard boxes lined with perforated polythene bags at −1° C. until use. For different experiments, the fruits were removed from cold storage, surface sterilized with 0.105% sodium hypochlorite (Clorox, Oakland, Calif.) for 2 min, rinsed with running tap water, then air dried. Two puncture wounds (6 mm in diameter and 3 mm deep) were made about 3.5 cm apart on each fruit midway along the calyx-stem end axis. After wounding, fruits were inoculated within 30 min. In all experiments d'Anjou pears were used, except for the side rot trial, in which Bosc pears were used. Side rot is a problem primarily on Bosc pears (Sugar, "The disease cycle of side rot of pear, caused by *Phialophora malorum*," Ph.D. thesis, Oregon State University, 1990).

Biocontrol Yeasts.

Thirty-one morphologically distinct strains of yeasts isolated from the surface of pear fruits by the method described above were stored at $-70°$ C. These strains were activated by dispensing 70 µl of suspension into 70 ml of yeast malt dextrose broth (YMDB; consisting of 3.0 g Bacto yeast extract, 3.0 g Difco malt extract, 5.0 g Bacto peptone and 10.0 g Bacto dextrose per liter) in a 200 ml flask. The yeast suspensions were incubated on a rotary shaker (125 rpm) for 48 h at $23°\pm1°$ C. The suspension (0.1 ml per Petri dish) was spread on yeast malt dextrose agar (YMDA) medium (composition was similar to YMDB; 18.0 g Bacto agar liter$^{-1}$ was added to solidify the medium). After 48 h of incubation at $23°\pm1°$ C., yeast growth from a Petri dish of each strain was removed with a sterile rubber policeman, suspended in 50 ml of sterile distilled water (SDW), and vortexed for 1 to 3 min. The yeast cells were centrifuged at $1.0\times10^4$ rpm for 15 min and the supernatant was discarded. The cells were resuspended in SDW and the concentration was adjusted to 8.0 to $12.0\times10^5$ cells per ml (70% transmittance at 550 nm using a Spectronic-20 spectrophotometer (Bausch and Lomb Optical Co., Rochester, N.Y.).

From the initial screening of 31 yeast strains, four yeast strains that gave the best control of blue mold of pears were selected: *Cryptococcus laurentii* strain HRA-5; *Rhodotorula aurantiaca* strain YCL5 and *Rhodotorula glutinis* strains HRA-4 and HRB-6. The efficacy of these yeast strains in controlling blue mold was further tested using 1.6 to $2.4\times10^6$ cells per ml (50% transmittance at 550 nm).

Of these fours strains, two strains, *Cryptococcus laurentii* strain HRA-5 and *Rhodotorula glutinis* strain HRB-6, were selected for further testing for control of blue mold when used alone or combined with a low dose of the fungicide thiabendazole (Mertect 340F, 15 µg ai ml$^{-1}$). Testing was conducted at $5°$, $10°$ and $20°$ C., using $1.5-2.0\times10^7$ yeast cells per ml (6% transmittance at 550 nm).

*Cryptococcus laurentii* strain HRA-5, *Rhodotorula glutinis* strain HRB-6, and *Cryptococcus infirmo-miniatus* strain YY-6 were screened for control of gray mold, Mucor rot, bull's-eye rot, and side rot of pear using 4.0 to $8.0\times10^7$ yeast cells per ml (2% transmittance at 550 nm). *Cryptococcus infirmo-miniatus* strain YY-6 was included because it showed the greatest effectiveness in controlling blue mold on Golden Delicious apples.

Pathogens.

*Penicillium expansum* (strain 46), *Botrytis cinerea* (strain 62), *Mucor piriformis* (strain 57, ATCC #60988), *Phialophora malorum* (strain 47) and *Pezicula malicorticis* (strain 14) were grown on potato-dextrose agar at $22°\pm1°$ C. After 7 to 8 days of incubation, a spore suspension of *Penicillium expansum* was made in SDW containing 0.005% Tween-80, filtered through a double layer of sterile muslin cloth, sonicated for 5 min (Model T14, L & R Manufacturing Co., Kearny, N.J.) to break spore chains into individual spores, and vortexed for 1 min to assure uniform mixing. For making the suspension of *B. cinerea*, the same procedure was used, except that 14-day-old cultures were used. Spore suspensions of *Mucor piriformis* and other two pathogens were made in SDW (without Tween-80 and sonication) after 7 and 14 days of incubation, respectively. Spore concentrations were determined with a hemacytometer and suspensions were used within 2–3 h. The concentrations of *Penicillium expansum*, *Botrytis cinerea*, *Mucor piriformis*, *Phialophora malorum* and *Pezicula malicorticis* used were: $5.0\times10^3$, $2.0\times10^3$, $2.0\times10^3$, $4.0\times10^3$, and $4.0\times10^3$, respectively.

Fruit Treatment.

Wounded fruits were placed on cardboard trays and each wound was inoculated with 50 µl of the fungus spore suspension. The pathogenicity of 31 strains of yeasts on pears and their efficacy in controlling blue mold was tested by inoculating a treatment mixture (yeast alone, yeast mixed with *P. expansum*, and *P. expansum* alone as control) into wounds on five pear fruit per treatment. Inoculated fruits were randomized, placed in cardboard boxes, incubated for 4 days at $5°$ C., then incubated for 6–7 days at $22°$ C. before recording disease incidence (% of inoculated wounds that developed rot) and severity (average rot diameter of diseased wound sites). Four yeasts that showed good potential in controlling blue mold were studied further. The efficacy of these yeasts in controlling blue mold was further tested using the method described above, except that each treatment had three replicates of five fruits each.

*Cryptococcus laurentii* and *Rhodotorula glutinis* were studied further for controlling blue mold at $5°$, $10°$ and $20°$ C. Treatment mixtures (i.e., yeast mixed with a pathogen, yeast integrated with a low concentration of the fungicide thiabendazole [15 µg ml$^{-1}$] and mixed with a pathogen, a mixture of the pathogen and a low or high concentration (525 µg ml$^{-1}$, as commercially recommended) of thiabendazole, and the pathogen alone as control] were applied in the wounds of pear fruits. There were three replications of ten fruits per treatment. Trays with inoculated fruits were randomized and placed in cardboard boxes lined with perforated polythene bags. Disease incidence and disease severity of blue mold were recorded after 6 to 7, 19 to 20 and 38 to 40 days of incubation at $5°$, $10°$ and $22°$ C. storage, respectively.

As described above, treatment mixtures of yeasts with *Botrytis cinerea*, *Mucor piriformis*, *Pezicula malicorticis* and *Phialophora malorum* were made and applied into the wounds on pears.

For Mucor rot and gray mold, there were three replications of three fruits per treatment for fruits incubated for 6 to 7 days at $22°\pm1°$ C. There were 20 fruits per replication for fruits incubated for 30 and 60 days at $-1°$ C. The experiments were repeated three times with three replications of 20 fruits per treatment with *Cryptococcus infirmo-miniatus* at $22°\pm1°$ C. For bull's-eye rot and side rots there were three replications of three fruits per treatment, and treated fruits were incubated for 30 days at $10°\pm1°$ C. before recording disease data.

Statistical Analysis.

Disease incidence was determined as the percentage of inoculated wounds that developed lesions. Percent data were subjected to arcsine-square root transformation (Steel and Torrie, Principles and Procedures of Statistics, McGraw Hill, New York, 1980) before analysis of variance, and means were separated by Duncan's multiple range test (P=0.05).

Results.

All yeasts and yeast-like fungal strains reduced rot diameter of diseased wounds, but only seven (approximately 23%) of the strains (*Cryptococcus albidus* strain HRB-2, *C. infirmo-miniatus* strain YY-6, *C. laurentii* strain HRA-5, *Rhodotorula aurantiaca* strain YCL-5, and *R. glutinis* strains HRA-3, HRA-4 and HRB-6) reduced disease incidence of blue mold on pears (Table 5). *C. laurentii* strain HRA-5, *R. aurantiaca* strain YCL5, and *R. glutinis* strains HRA-4 and HRB-6 were most effective in reducing disease incidence and severity. Control of blue mold of pears using *C. infirmo-miniatus*, *R. aurantiaca* and *R. glutinis* has not been previously reported (Wisniewski and Wilson, Hort-Science 27: 94–98, 1992). It is important to note that most of the yeast strains, particularly those in the genus Cryptococcus, were not effective biocontrol agents in this test.

None of the yeasts caused any disease in the inoculated fruits, even when the fruits were incubated for 15 days at 22°±2° C. The lesion diameter seldom exceeded 10 mm, even when inoculated fruits were incubated for 13–15 days at 22° C.

*C. laurentii* strain HRA-5 and *R. glutinis* strain HRB-6 were most effective in reducing disease incidence and significantly reduced the severity of blue mold on inoculated fruits (Table 6). None of the fruit inoculated with a yeast suspension alone developed disease. *C. laurentii* and *R. glutinis* performed better for blue mold control of pears than in preliminary tests presented in Table 5. This may be due to higher numbers of yeast cells per ml in the inoculation mixture than were used in the preliminary tests. Similarly, the efficacy of a yeast (*Candida sp.*) in controlling blue and gray mold of Golden Delicious apples has been reported to increase with increased concentration of yeast cells (McLaughlin et al., Phytopathol. 80:456–461, 1990).

Based on these results, *C. laurentii* strain HRA-5 and *R. glutinis* strain HRB-6 were tested alone and in combination with a low dose (15 µg ml$^{-1}$) of thiabendazole for the control of blue mold at 5°, 10° and 20° C. The yeasts alone or in combination with thiabendazole significantly reduced blue mold incidence and severity at all temperatures (Tables 7 and 8).

The combination of yeasts with a low dose of thiabendazole gave significantly better disease control at all temperatures than the low dose of thiabendazole alone and was comparable to disease control achieved using a high dose of thiabendazole. Using this approach, thiabendazole residues can be reduced by about 97% or more and still achieve excellent control of blue mold. This approach is especially attractive to reduce thiabendazole residues on food. Under packinghouse conditions, *P. expansum* populations consist of benzimidazole-sensitive and insensitive strains (Spotts and Cervantes, Plant Dis. 70:106–108, 1986). Under such conditions, for example, the yeast-thiabendazole combination protects against blue mold better than thiabendazole alone, even at high concentrations.

The efficacy of *C. laurentii*, *R. glutinis* and *C. infirmo-miniatus* alone and combined with a low dose of thiabendazole against Mucor rot was determined. All of these yeasts alone or when combined with a low dose of thiabendazole significantly reduced disease incidence and severity at −1° and 20° C. Thiabendazole alone (low and high concentrations) failed to provide any protection against Mucor rot (Table 9). Benzimidazole fungicides have been reported to be ineffective in controlling Mucor rot (Maculates and Sports, Plant Dis. 74:537–543, 1990). In most cases, a combination of a yeast and a low dose of thiabendazole was not significantly better in controlling disease than yeast alone, probably due to insensitivity of *Mucor piriformis* to benzimidazole fungicides. *C. infirmo-miniatus* was significantly better than all other treatments in reducing the incidence of Mucor rot; disease incidence was reduced from 100% to 42% at −1° C. and from 100% to 11% at 20° C. (Table 10). The effectiveness of these yeasts against Mucor rot, especially *Cryptococcus infirmo-miniatus*, is especially significant since all fungicides currently registered for postharvest treatment of pome fruits are ineffective against *Mucor piriformis* (Maculates and Spotts, Plant Dis. 74:537–543, 1990).

The efficacy of *C. infirmo-miniatus* was tested in three different trials to confirm its effectiveness in the biological control of Mucor rot (Table 10). In all trials *C. infirmo-miniatus* significantly reduced disease incidence and severity. The reduction in disease incidence varied from 62 to 89 percent, whereas the diameters of diseased wounds were reduced from 40.3 to 5.3, 28.3 to 8.8 and 31.3 to 8.6 in trials 1, 2 and 3, respectively. This is the first report documenting the biological control potential of *C. infirmo-miniatus* against Mucor rot.

All treatments significantly reduced gray mold incidence and severity on pears at −1° C. When yeasts were integrated with a low dose of thiabendazole, the reduction in gray mold incidence was not significantly different from the fruits treated with a high dose of thiabendazole alone and stored at −1° and 20° C. (Table 11). Fruits with apparently healthy wounds after 60 days of storage at −1° C. were ripened for 5 days at 20° C., and more than 95% of the wounds remained healthy. It usually takes 45 to 60 days at −1° C. for pear wounds to heal. Probably due to wound healing, gray mold incidence did not increase. In the case of Mucor rot, approximately 50% of apparently healthy wounds (after 30 days of fruit storage at −1° C.) developed rot when incubated for five days at 20° C., indicating survival of the pathogen and partial wound healing. All yeasts were more effective in reducing disease severity when integrated with a low dose of thiabendazole than alone. For the first time we report the control of gray mold of pears using three yeast *C. laurentii*, *R. glutinis* and *C. infirmo-miniatus*.

Side rot of Bosc pears was completely controlled by all yeasts alone or when integrated with a low dose of thiabendazole (Table 12). Thiabendazole (15 and 525 µg ml$^{-1}$) was ineffective in reducing disease incidence and severity due to insensitivity of *P. malorum* to benzimidazole fungicides (Sugar et al., Plant Dis. 78:791–795, 1994). This is the first report of control of side rot of pears with *R. glutinis* or *C. infirmo-miniatus*.

All yeasts alone or when integrated with a low dose of thiabendazole significantly reduced the incidence and severity of bull's-eye rot (Table 12). Yeasts, when integrated with a low dose of thiabendazole, completely controlled bull's-eye rot, and control was not significantly different than using the high dose of thiabendazole (Table 12). There are apparently no previously published reports on the control of bull's-eye rot using biological control agents.

It is important to note that most of the yeast strains tested, particularly those in the genus Cryptococcus, were determined to be ineffective biocontrol agents. There are significant differences among strains of even a single species of yeast in their effectiveness in controlling fungal disease.

TABLE 5

Efficacy$^w$ of yeasts and yeast-like fungal colonists of pears, isolated from different locations of the Pacific Northwest of the United States, in controlling blue mold of d'Anjou pears.

| Treatment | Location$^x$ | Cultivar | Yeast isolate | Pathogenicity$^y$ | DI$^z$ | DS$^z$ |
|---|---|---|---|---|---|---|
| *Aureobasidium pullulans* | HR | Anjou | HRA1 | + | 100 | 19.5 |
| | | | HRA2 | + | 100 | 17.8 |
| | | Bartlett | HRB1 | + | 100 | 19.0 |
| | | | HRB4 | + | 100 | 20.3 |

TABLE 5-continued

Efficacy[w] of yeasts and yeast-like fungal colonists of pears, isolated from different locations of the Pacific Northwest of the United States, in controlling blue mold of d'Anjou pears.

| Treatment | Loca-tion[x] | Cultivar | Yeast isolate | Pathoge-nicity[y] | DI[z] | DS[z] |
|---|---|---|---|---|---|---|
|  | CL | Bartlett | YCL1 | + | 100 | 20.9 |
|  | M | Bosc | YMB1 | + | 100 | 26.7 |
|  |  |  | YMB3 | + | 100 | 27.4 |
|  | Y | Bartlett | YY1 | + | 100 | 25.2 |
|  |  |  | YY4 | + | 100 | 21.5 |
| Cryptococcus albidus | HR | Bartlett | HRB2 | – | 90 | 16.4 |
|  | CL | Bartlett | YCL2 | – | 100 | 19.4 |
|  | M | Bosc | YMB2 | – | 100 | 23.1 |
|  | Y | Bartlett | YY2 | – | 100 | 20.5 |
|  |  |  | YY8 | – | 100 | 19.9 |
| Cryptococcus infirmo-miniatus | HR | Bartlett | HRB7 | – | 100 | 17.5 |
|  | Y | Bartlett | YY6 | – | 90 | 19.9 |
|  |  |  | YY7 | – | 100 | 25.7 |
| Cryptococcus laurentii | HR | Anjou | HRA5 | – | 80 | 13.2 |
|  |  |  | HRB3 | – | 100 | 21.8 |
|  | Y | Bartlett | YY3 | – | 100 | 24.8 |
| Debaryomyces hansenii | CL | Bartlett | YCL4 | – | 100 | 23.9 |
| Rhodotorula aurantiaca | CL | Bartlett | YCL5 | – | 50 | 15.8 |
| Rhodotorula fujisanensis | CL | Bartlett | YCL3 | – | 100 | 25.9 |
| Rhodotorula glutinis | HR | Anjou | HRA3 | – | 90 | 16.1 |
|  |  |  | HRA4 | – | 90 | 12.1 |
|  |  | Bartlett | HRB5 | – | 100 | 21.9 |
|  |  |  | HRB6 | – | 80 | 14.0 |
|  | M | Bosc | YMB4 | – | 100 | 25.3 |
| Rhodotorula minuta | HR | Bartlett | HRA6 | – | 100 | 17.6 |
|  | CL | Bartlett | YCL7 | – | 100 | 21.0 |
| Sporobolomyces roseus | CL | Bartlett | YCL6 | – | 100 | 21.9 |
| Penicillium expansum alone |  |  |  |  | 100 | 35.5 |

[w]The wounds were treated with a spore suspension (5.0 × 10³ ml⁻¹) of *Penicillium expansum* alone or a mixture of yeast suspension (8.0–12.0 × 10⁵ cells ml⁻¹) and *Penicillium expansum*. Data were recorded after 4 days of incubation at 5° C. followed by 6–7 days of incubation at 22 ± 2° C.
[x]HR, Hood River (Oregon); CL, Cascade Locks (Oregon); M, Medford (Oregon) and Y, Yakima (Washington).
[y]+, yeast alone caused dry rot at the inoculated wound sites. –, yeast alone caused no disease at the inoculated wound sites.
[z]Disease incidence (DI) is the percent of treated wounds that developed rot. Disease severity (DS) is rot diameter (mm) of diseased wounds.

TABLE 6

Efficacy[y] of 4 yeast isolates in controlling blue mold of d'Anjou pears.

| Treatment | Isolate | DI[z] | DS[z] |
|---|---|---|---|
| C. laurentii | HRA5 | 68a | 14.8a |
| R. aurantiaca | YCL5 | 92bc | 16.7a |
| R. glutinis | HRA4 | 82ab | 15.2a |
| R. glutinis | HRB6 | 68a | 15.8a |
| Penicillium expansum alone |  | 46 | 100c | 31.1b |

[y]The wounds were treated with a spore suspension (5.0 × 10³ spores ml⁻¹) of *Penicillium expansum* or a mixture of yeast suspension (8.0–12.0 × 10⁵ ml⁻¹) and *Penicillium expansum*. Data were recorded after 6–7 days of incubation at 22 ± 2° C.
[z]Disease incidence (DI) is the percent of treated wounds that developed rot. Disease severity (DS) is rot diameter (mm) of diseased wounds. Within a column, values with the same letters are not significantly different at P = 0.05 according to Duncan's multiple range test.

TABLE 7

Efficacy[y] of *Cryptococcus laurentii* (isolate HRA5) and *Rhodotorula glutinis* (isolate HRB6) alone or in the presence of a reduced rate of thiabendazole (TBZ) in controlling incidence of blue mold of pears caused by *Penicillium expansum*.

| | Diseased wounds (%)[z] | | | | | |
|---|---|---|---|---|---|---|
| | 5° C. | | 10° C. | | 20° C. | |
| Treatment | 1993 | 1994 | 1993 | 1994 | 1993 | 1994 |
| C. laurentii | 0a | 13b | 7b | 43b | 47b | 50b |
| C. laurentii + TBZ | 0a | 0a | 0a | 7a | 0a | 7a |
| R. glutinis | 7b | 10b | 17c | 33b | 53b | 47b |
| R. glutinis + TBZ | 0a | 0a | 0a | 3a | 3a | 3a |
| TBZ (15 µg ml⁻¹) | 7b | 40c | 13bc | 43b | 73c | 93c |
| TBZ (525 µg ml⁻¹) | 0a | 0a | 0a | 3a | 0a | 3a |
| P. expansum alone | 53c | 93d | 83d | 100c | 100c | 100c |

[y]The wounds were treated with a spore suspension of *P. expansum* (5.0 × 10³ ml⁻¹) alone, a mixture of TBZ (15 and 525 µg ml⁻¹) and *P. expansum*, or yeast suspension (2.0–3.0 × 10⁷ cells ml⁻¹) and *P. expansum* with a reduced rate of TBZ or without it. Data were recorded after 35–40, 17–20, and 6–8 days of incubation at 5, 10 and 20° C., respectively.
[z]Within a column, values with the same letters are not significantly different at P = 0.05 according to Duncan's multiple range test.

TABLE 8

Efficacy[y] of *Cryptococcus laurentii* (isolate HRA5) and *Rhodotorula glutinis* (isolate HRB6) alone or in the presence of a reduced rate of thiabendazole (TBZ) in controlling severity of blue mold on pears caused by *Penicillium expansum*.

| | Lesion diameter (mm)[z] | | | | | |
|---|---|---|---|---|---|---|
| | 5° C. | | 10° C. | | 20° C. | |
| Treatment | 1993 | 1994 | 1993 | 1994 | 1993 | 1994 |
| C. laurentii | NI | 7.6a | 14.7a | 15.6b | 13.0b | 9.4a |
| C. laurentii + TBZ | NI | NI | NI | 5.3a | NI | 5.7a |
| R. glutinis | 4.4a | 4.8a | 26.3ab | 18.5b | 13.6b | 10.2a |
| R. glutinis + TBZ | NI | NI | NI | 3.6a | 2.3a | 4.3a |
| TBZ (15 µg ml⁻¹) | 6.3a | 11.6b | 39.0b | 19.8b | 30.3c | 24.5b |
| TBZ (525 µg ml⁻¹) | NI | NI | NI | 3.3a | NI | 5.6a |
| P. expansum alone | 23.5b | 26.5c | 40.7c | 37.2c | 33.3c | 32.0b |

[y]The wounds were treated with a spore suspension of *P. expansum* (5.0 × 10³ ml⁻¹), a mixture of TBZ (15 and 525 µg ml⁻¹) and *P. expansum*, or yeast suspension (2.0–3.0 × 10⁷ cells ml⁻¹) and *P. expansum* with a reduced rate of TBZ or without it. Data were recorded after 35–40, 17–20, and 6–8 days of incubation at 5, 10 and 20° C., respectively.
[z]Within a column, values with the same letters are not significantly different at P = 0.05 according to Duncan's multiple range test.

TABLE 9

Efficacy[y] of *Cryptococcus laurentii* (isolate HRA5), *Rhodotorula glutinis* (isolate HRB6), and *Cryptococcus infirmo-miniatus* (isolate YY6) alone or in the presence of a reduced rate of thiabendazole (TBZ) in controlling Mucor rot caused by *Mucor piriformis* at −1 and 20° C.

| | −1° C. | | 20° C. | |
|---|---|---|---|---|
| Treatment | DI[z] | DS[z] | DI | DS |
| C. laurentii | 92cd | 17.7c | 82bc | 20.9b |
| C. laurentii + TBZ | 83bc | 15.4bc | 72b | 26.9bc |
| R. glutinis | 70b | 14.9bc | 83bc | 26.0bc |
| R. glutinis + TBZ | 76b | 16.6c | 83bc | 25.2bc |
| C. infirmo-miniatus | 49a | 12.5b | 11a | 5.3a |
| C. infirmo-miniatus + TBZ | 42a | 7.9a | 11a | 7.7a |
| TBZ (15 µg ml⁻¹) | 97de | 29.0d | 94c | 31.7cd |

TABLE 9-continued

Efficacy[y] of *Cryptococcus laurentii* (isolate HRA5), *Rhodotorula glutinis* (isolate HRB6), and *Cryptococcus infirmo-miniatus* (isolate YY6) alone or in the presence of a reduced rate of thiabendazole (TBZ) in controlling Mucor rot caused by *Mucor piriformis* at −1 and 20° C.

|  | −1° C. | | 20° C. | |
|---|---|---|---|---|
| Treatment | DI[z] | DS[z] | DI | DS |
| TBZ (525 μg ml⁻¹) | 98de | 28.4d | 100c | 32.2cd |
| *Mucor piriformis* alone | 100e | 29.8d | 100c | 40.6d |

[y]The wounds were treated with a spore suspension (2.0 × 10³ ml⁻¹) of *M. piriformis*, a mixture of TBZ (15 and 525 μg ml⁻¹) and *M. piriformis*, or yeast suspension (1.4–1.6 × 10⁸ cells ml⁻¹) and *M. piriformis* mixed with a reduced rate of TBZ or without it. Data were recorded after 30 and 6–7 days of incubation at −1 and 22° C., respectively.
[z]Disease incidence (DI) is the percent of treated wounds that developed rot. Disease severity (DS) is rot diameter (mm) of diseased wounds. Within a column, values with the same letters are not significantly different at P = 0.05 according to Duncan's multiple range test.

TABLE 10

Efficacy[y] of *Cryptococcus infirmo-miniatus* (isolate YY6) in controlling Mucor rot caused by *Mucor piriformis* at 22° C.

|  | Trial 1 | | Trial 2 | | Trial 3 | |
|---|---|---|---|---|---|---|
| Treatment | DI[z] | DS[z] | DI | DS | DI | DS |
| *C. infirmo-miniatus* | 11a | 5.3a | 38a | 8.8a | 23a | 8.6a |
| *Mucor piriformis* alone | 100b | 46.3b | 100b | 28.3b | 100b | 31.3b |

[y]The wounds were treated with a spore suspension (2.0 × 10³ ml⁻¹) of *Mucor piriformis* or with a mixture of yeast suspension (1.4–1.6 × 10⁸ cells ml⁻¹) and *M. piriformis*. Disease data were recorded after 6–7 days of incubation at 22° C.
[z]Disease incidence (DI) is the percent of treated wounds that developed rot. Disease severity (DS) is rot diameter (mm) of diseased wounds. Within a column, values with the same letters are not significantly different at P = 0.05 according to Duncan's multiple range test.

TABLE 11

Efficacy[y] of *Cryptococcus laurentii* (isolate HRA5), *Rhodotorula glutinis* (isolate HRB6), and *Cryptococcus infirmo-miniatus* (isolate YY6) alone or in the presence of a reduced rate of thiabendazole (TBZ) in controlling gray mold caused by *Botrytis cinerea* at −1 and 20° C.

|  | −1° C. | | 20° C. | |
|---|---|---|---|---|
| Treatment | DI[z] | DS[z] | DI | DS |
| *C. laurentii* | 65c | 34.3cd | 44c | 19.4b |
| *C. laurentii* + TBZ | 3a | 22.0bcd | 17ab | 7.0a |
| *R. glutinis* | 57c | 36.0d | 44c | 14.4ab |
| *R. glutinis* + TBZ | 2a | 14.7ab | 17ab | 12.0ab |
| *C. infirmo-miniatus* | 65c | 30.9bcd | 22b | 9.0a |
| *C. infirmo-miniatus* + TBZ | 3a | 17.1abc | 11ab | 5.6a |
| TBZ(15 μg ml⁻¹) | 35b | 33.1cd | 100d | 35.8c |
| TBZ(525 μg ml⁻¹) | 0a | NI | 6a | 6.6a |
| *Botryis cinerea* alone | 100d | 83.6e | 100d | 40.7c |

[y]The wounds were treated with a spore suspension (2.0 × 10³ ml⁻¹) of *B. cinerea*, a mixture of TBZ (15 and 525 μg ml⁻¹) and *B. cinerea*, or yeast suspension (1.4–1.6 × 10⁸ cells ml⁻¹) and *B. cinerea* with a reduced rate of TBZ or without it. Data were recorded after 60 and 6–7 days of incubation at −1 and 22° C.
[z]Disease incidence (DI) is the percent of treated wounds that developed rot. Disease severity (DS) is rot diameter (mm) of diseased wounds. No visual infection (NI) at inoculated wound sites. Within a column, values with the same letters are not significantly different at P = 0.05 according to Duncan's multiple range test.

TABLE 12

Efficacy of *Cryptococcus laurentii* (isolate HRA5), *Rhodotorula glutinis* (isolate HRB6), and *Cryptococcus infirmo-miniatus* (isolate YY6) alone or in the presence of a reduced rate of thiabendazole (TBZ) in controlling side rot of Bosc pears and bull's-eye rot of d'Anjou pears caused by *Phialophora malorum* and *Pezicula malicorticis*, respectively.

|  | *P. malorum* | | *E. malicorticis* | |
|---|---|---|---|---|
| Treatment | DI[z] | DS[z] | DI | DS |
| *C. laurentii* | 5a | 2.0a | 11b | 5.3ab |
| *C. laurentii* + TBZ | 5a | 1.7a | 0a | NI |
| *R. glutinis* | 0a | NI | 5ab | 2.7a |
| *R. glutinis* + TBZ | 0a | NI | 0a | NI |
| *C. infirmo-miniatus* | 0a | NI | 11b | 4.3ab |
| *C. infirmo-miniatus* + TBZ | 0a | NI | 0a | NI |
| TBZ (15 μg ml⁻¹) | 72b | 7.4b | 56c | 8.6bc |
| TBZ (525 μg ml⁻¹) | 72b | 7.7b | 0a | NI |
| Fungal pathogen alone | 80b | 8.8b | 100d | 12.2c |

[y]The wounds were treated with a fungal (4.0 × 10³ spores ml⁻¹) pathogen alone, a mixture of TBZ (15 and 525 μg ml⁻¹)) and a fungal pathogen, or yeast suspension (1.4–1.6 × 10⁸ cells ml⁻¹) and a fungal pathogen with a reduced rate of TBZ or without it. Data were recorded after 30 days of incubation at 10° C.
[z]Disease incidence (DI) is the percent of treated wounds that developed rot. Disease severity (DS) is rot diameter (mm) of diseased wounds. No visual infection (NI) at inoculated wound sites. Within a column, values with the same letters are not significantly different at P = 0.05 according to Duncan's multiple range test.

Example 3

Control of Postharvest Blue Mold of Apples Using Natural Saprophytic Yeast Colonists Fruits.

Apple fruits (cv. Golden Delicious) grown at the Mid-Columbia Agricultural Research and Extension Center in Hood River, Oreg., were harvested in the second week of September during 1993 and 1994. At harvest, fruit firmness was 55±2 and 50±2 Newtons (0.225 lb. per Newton) and percent soluble solids were 12.0±2 and 13±1.5, in 1993 and 1995, respectively. Firmness was determined with a UC pressure test penetrometer (Ametek, Bellingham, Wash.) and soluble solids using a hand refractometer (VWR Scientific, Los Angeles, Calif.). Fruits were stored at 0° C. in cardboard boxes lined with perforated polythene bags until use.

On each apple, two puncture wounds (6 mm in diameter and 3 mm deep) were made about 3.5 cm apart midway along the calyx-stem axis. After wounding, apple fruits were inoculated within 30 min.

Biocontrol Yeasts.

Six yeast strains (two strains of *Cryptococcus spp.* and four strains of *Rhodotorula spp.*) isolated from the surface of pear fruits and shown to control blue mold of pear as described above were selected for the apple studies. Yeasts were stored at −70° C. and were activated by dispensing 70 μl of suspension into 70 ml of yeast malt dextrose broth (YMDE; consisting of 3.0 g Bacto yeast extract, 3.0 g Difco malt extract, 5.0 g Bacto peptone and 10.0 g Bacto dextrose liter⁻¹ of medium) in a 200 ml flask. Yeast suspensions were incubated on a rotary shaker at 125 rpm for 48 hours at 23°±1° C. The suspension (0.1 ml per Petri dish) was spread on yeast malt dextrose agar (YMDA) medium (similar to YMDB, except 18.0 g Bacto agar liter⁻¹ was added to solidify the medium). After 48 hours of incubation at 23°±1° C., yeast growth was removed with a sterile rubber policeman, suspended into 50 ml of sterile distilled water (SDW), and vortexed for 1–3 minutes. The yeast cells were centrifuged at 1.0×10⁴ rpm for 15 minutes and the supernatant was discarded. The cells were resuspended in SDW, and the concentration was adjusted to $1.6-2.4 \times 10^6$ cells per ml (50% transmittance at 550 nm using a spectrophotometer model Spectronic 20, Bausch and Lomb Optical Co., Rochester, N.Y.).

From the initial screening of six yeast strains, two yeast strains, *Cryptococcus infirmo-miniatus* strain YY6 and *C. laurentii* strain HRA5, gave the best control of blue mold of apples. The efficacy of either of these yeasts alone or when integrated with a low dose of the fungicide thiabendazole (TBZ, Mertect 340F, 15 µg ai ml$^{-1}$) was tested for control of blue mold at 5°, 10° and 20° C. using $2.0-3.0 \times 10^7$ yeast cells per ml (6% transmittance at 550 nm).

Pathogens.

*Penicillium expansum* strain 46 was grown on potato dextrose agar at 22°±1° C. After 7–8 days of incubation, a spore suspension was made in SDW containing 0.005% Tween-80 (SDWT), filtered through a double layer of sterile muslin cloth, sonicated for 5 minutes (Model T14, L&R Manufacturing Co., Kearny, N.J.) to break spore chains into individual spores, and vortexed for one minute to assure uniform mixing. Spore concentrations were determined with a hemacytometer, and suspensions were used within two to three hours.

During the course of this investigation the concentration of *Penicillium expansum* used was $5.0 \times 10^3$ spores/ml.

Fruit treatment.

The efficacy of six strains of yeasts for control of blue mold was tested by inoculating wounded apple fruits with 50 µl per wound of yeast alone, yeast mixed with *P. expansum*, and *P. expansum* alone as control. There were five replications of five fruits per treatment. Trays with inoculated fruits were randomized and placed in cardboard boxes lined with perforated polythene bags. Fruits were incubated for 7–8 days at 22° C. before recording disease incidence (percentage of inoculated wounds that developed rot) and severity (average rot diameter of diseased wound sites).

Two yeasts, *Cryptococcus infirmo-miniatus* and *C. laurentii*, showed the greatest potential for control of blue mold and were selected for further studies. The efficacy of these two yeasts for control of blue mold at 5°, 10° and 20° C. was tested. The following treatment mixtures were applied in the wounds of apple fruits: *P. expansum* alone, a mixture of TBZ (15 and 525 µg ml$^{-1}$ and *P. expansum*, or yeast suspension and *P. expansum* with the low rate of TBZ or without it. There were three replications of five fruits per treatment. Trays with inoculated fruits were randomized and placed in cardboard boxes lined with perforated polythene bags. Incidence and severity of blue mold were recorded after 6–8, 17–20 and 35–40 days of incubation at 5°, 10° and 20° C., respectively.

Population Studies of Yeasts in Wounds.

The ability of yeast cells to survive and multiply in apple wounds was studied to determine if these yeasts were effective colonizers. Fruits were wounded, then inoculated with 50 µl of a suspension containing $2 \times 10^7$ yeast cells ml$^{-1}$. Fruits were incubated in plastic boxes at 0°, 5°, 10° and 20° C. Viable cell concentrations of the inoculum were determined by a modified dilution plate frequency technique (Chand et al., Appl. Environ. Microbiol. 58:3374–3379, 1992). Individual fruits served as one replicate in a randomized complete block design, and three replicates were sampled at each time and temperature. For the fruits incubated at 5°, 10° and 20° C., the wounds were sampled 0, 1, 2, 3, 4 and 7 days after inoculation, whereas at 0° C., samples were removed 0, 3, 10, 15 and 30 days after inoculation. Samples were taken using a cork borer (10 mm internal diameter) and macerated in distilled sterile water. Serial dilutions were plated in duplicate on YMDA using the modified dilution plate frequency technique.(Chand et al., 1992) and incubated at 22°±2° C for 4 days when yeast populations were determined and expressed as $\log_{10}$ CFU per wound.

Statistical Analysis.

Disease incidence was the percentage of inoculated wounds that developed lesions. Percent data were subjected to arsine-square root transformation (Steel and Torrie, Principles and Procedures of Statistics, p. 158, McGraw-Hill, New York, 1980) before analysis of variance, and means were separated by Duncan's multiple range test (P=0.05). Disease severity was the rot diameter of diseased wound sites and was statistically analyzed with the method above for incidence.

Results.

All six yeasts significantly reduced both incidence and severity of blue mold on apple fruit (Table 13). When both of these measures of disease were considered, *C. infirmo-miniatus* and *C. laurentii* were the most effective of the six yeasts, and these two were selected for further study.

Control of blue mold of apple with *C. infirmo-miniatus* and *C. laurentii* was evaluated at 5°, 10°, and 20° C. At 5° C., both yeasts alone and with TBZ reduced the incidence of blue mold, and there were no significant differences (P=0.05) between biocontrol treatments (Table 14). At 10° C., *C. laurentii* alone and TBZ at 15 µg ml$^{-1}$ were less effective than other treatments; differences were significant (P=0.05) in 1993, but not in 1994. At 20° C., a treatment with either yeast alone or either yeast together with a low dose of TBZ alone was less effective than a treatment employing one of the yeasts together with TBZ or a high dose of TBZ alone. However, either yeast alone or either yeast together with a low dose of TBZ provided a significant reduction of incidence of blue mold when compared with the control (*P. expansum* alone) (Table 14). Disease incidence was greater in 1993 than in 1994. The effect of yeast treatments on severity of blue mold was similar to the effects on incidence (Table 15).

Figure 1B:
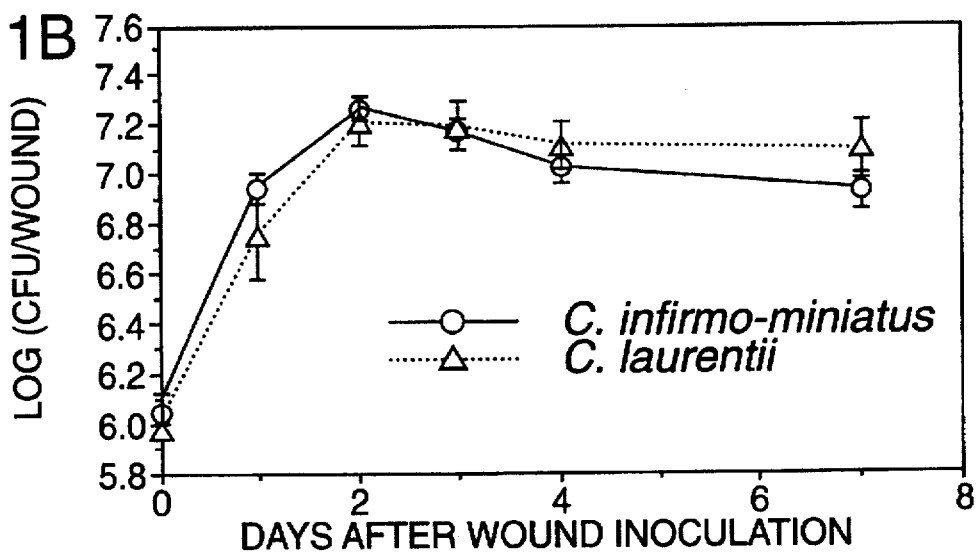
Figure 1C:
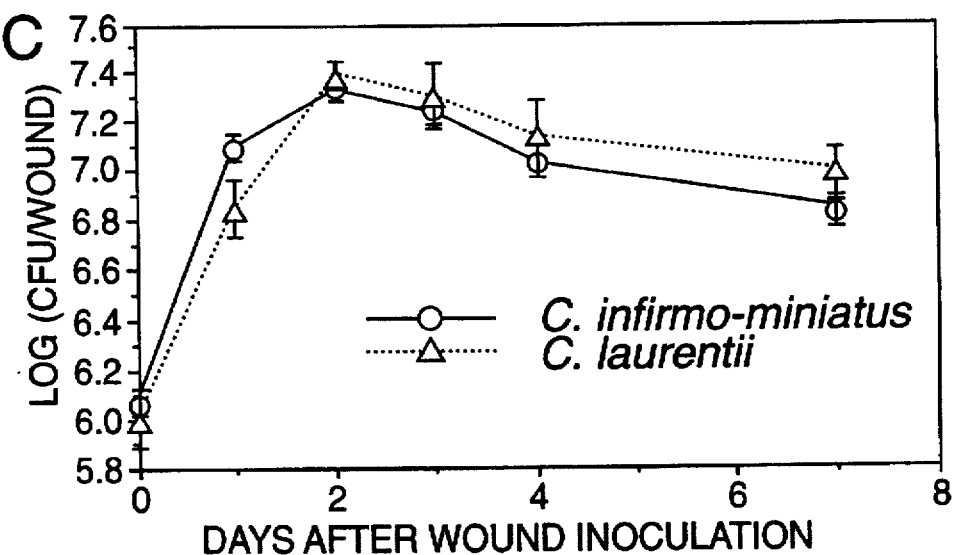
Figure 1D:
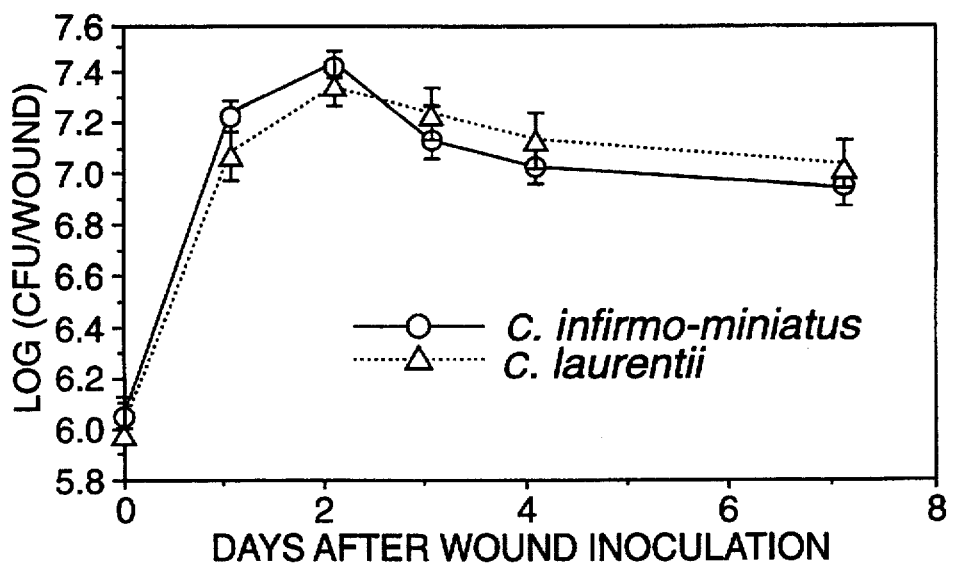

The population dynamics of the yeasts in apple wounds was studied at 0°, 5°, 10°, and 20° C. At 0° C., the populations of *C. infirmo-miniatus* and *C. laurentii* increased in 1log$_{10}$ units from about 6.6 to a maximum of about 7.8 per wound in 10 days (FIG. 1A). This was followed by a gradual decline to about 7.6–7.7 log units by day 30. A similar pattern was observed at temperatures between 5° C. and 20° C.: the populations of the yeasts increased about 1.4 log units to a maximum of 7.4 in the first two days (FIGS. 1B, 1C, and 1D). Yeast populations declined over the next five days to about 7.1 log units per wound.

The yeasts *C. infirmo-miniatus* and *C. laurentii* were thus shown to be effective in the biocontrol of blue mold of apple at 5° C., but were less effective at 10° C. or 20° C. when the yeasts were used alone. When *C. infirmo-miniatus* or *C. laurentii* were combined with TBZ at 15 µg ml$^{-1}$, excellent control was achieved at all temperatures and was equivalent to the full, labeled rate of TBZ. The low rates of TBZ and iprodione in this study represent reductions of 97 and 98%, respectively, of the full labeled rates (Willet et al., Postharvest Pomology Newsletter 7:1–15, 1989). Thus, a significant reduction in fungicide residues is possible with these combination treatments. Biocontrol over a wide temperature range is important with apples, because fruit are stored at 0° C. or slightly warmer (U.S. Dept. of Agriculture, Agriculture Research Service, The commercial storage of fruits, vegetables, and florist and nursery stocks, pp. 23–26, Agric. Handbook 291, 1968), then held at warmer temperatures in terminal markets.

Fruit maturity also effects susceptibility to decay (Pierson et al., Market diseases of apples, pears, and quinces, U.S. Dept. of Agriculture Handbook 376, U.S. Department of Agriculture, Agricultural Research Service, 1971, at p. 2). Apple fruit appeared to be considerably more susceptible in 1993 than in 1994 (Table 14). Nevertheless, the combination treatments of yeast with the low rate of TBZ controlled blue mold in both years.

In addition to varying temperatures and fruit maturity levels, apple fruit also are infected in the postharvest environment by a variety of pathogens (Pierson et al., 1971). As described above, *C. infirmo-miniatus* and *C. laurentii* control gray mold, bull's-eye rot, Mucor rot, and side rot of pear. These pathogens also affect apple fruit, and apples can be similarly treated with the yeast strains of the present invention alone or in combination with appropriate chemical fungicides.

Resistance of *P. expansum* to benzimidazoles has been reported (Wicks, Plant Dis. Reptr. 61:447–449, 1977). Because the mode of action of *C. infirmo-miniatus* and *C. laurentii* does not involve antibiosis, as discussed above, it is unlikely that resistance will develop to these yeasts.

TABLE 13

Efficacy[Y] of 6 yeast strains in controlling blue mold of Golden Delicious apples.

| Treatment | Strain | DI[z] | DS[z] |
|---|---|---|---|
| *C. infirmo-miniatus* | YY6 | 8a | 3.6a |
| *C. laurentii* | HRA5 | 12a | 3.7a |
| *R. aurantiaca* | YCL5 | 36ab | 10.3b |
| *R. glutinis* | HRA3 | 36ab | 11.8b |
| *R. glutinis* | HRA4 | 32ab | 10.5b |
| *R. glutinis* | HRB6 | 36ab | 8.6ab |
| *Penicillium expansum* alone | | 100c | 31.1c |

[Y]The wounds were treated with a spore suspension (5.0 × 10³ spores ml⁻¹) of *Penicillium expansum* or a mixture of yeast suspension (1.6–2.4 × 10⁶ ml⁻¹) and *Penicillium expansum*. Data were recorded after 7–8 days of incubation at 22 ± 2° C.
[z]Disease incidence (DI) is the percent of treated wounds that developed rot. Disease severity (DS) is rot diameter (mm) of diseased wounds. Within a column, values with the same letters are not significantly different at P = 0.05 according to Duncan's multiple range test.

TABLE 14

Efficacy[y] of *Cryptococcus infirmo-miniatus* (strain YY6) and *Cryptococcus laurentii* (strain HRA5) alone or in the presence of a reduced rate (15 μg ml⁻¹) of thiabendazole (TBZ) in controlling incidence of blue mold of Golden Delicious apples caused by *Penicillium expansum*.

| | Diseased wounds (%)[z] | | | | | |
|---|---|---|---|---|---|---|
| | 5° C. | | 10° C. | | 20° C. | |
| Treatments | 1993 | 1994 | 1993 | 1994 | 1993 | 1994 |
| *C. infirmo-miniatus* | 0a | 0a | 3a | 3a | 37bc | 7a |
| *C. infirmo-miniatus* + TBZ | 0a | 0a | 0a | 0a | 3a | 0a |
| *C. laurentii* | 3ab | 3ab | 37c | 10a | 56c | 17b |
| *C. laurentii* + TBZ | 0a | 0a | 3a | 0a | 3a | 0a |
| TBZ (15 ppm ai) | 7b | 7b | 13b | 10a | 23b | 17b |

TABLE 14-continued

Efficacy[y] of *Cryptococcus infirmo-miniatus* (strain YY6) and *Cryptococcus laurentii* (strain HRA5) alone or in the presence of a reduced rate (15 μg ml⁻¹) of thiabendazole (TBZ) in controlling incidence of blue mold of Golden Delicious apples caused by *Penicillium expansum*.

| | Diseased wounds (%)[z] | | | | | |
|---|---|---|---|---|---|---|
| | 5° C. | | 10° C. | | 20° C. | |
| Treatments | 1993 | 1994 | 1993 | 1994 | 1993 | 1994 |
| TBZ (525 ppm ai) | 0a | 0a | 0a | 0a | 3a | 0a |
| *P. expansum* | 43c | 33c | 97d | 67b | 100d | 87c |

[y]The wounds were treated with a spore suspension of *P. expansum* (5.0 × 10³ ml⁻¹) alone, a mixture of TBZ (15 and 525 ppm ai) and *P. expansum*, or yeast suspension (2.0–3.0 × 10⁷ ml⁻¹) and *P. expansum* with a reduced rate of TBZ or without it. There were three replicates of 5 fruits each per treatment. Data were recorded after 35–40, 17–20, and 6–8 days of incubation at 5, 10 and 20° C., respectively.
[z]Within a column, values with the same letters are not significantly different at P = 0.05 according to Duncan's multiple range test.

TABLE 15

Efficacy[y] of *Cryptococcus infirmo-miniatus* (strain YY6) and *Cryptococcus laurentii* (strain HRA5) alone or in the presence of a reduced rate (15 μg ml⁻¹) of thiabendazole (TBZ) in controlling severity of blue mold of Golden Delicious apples caused by *Penicillium expansum*.

| | Lesion diameter (mm)[z] | | | | | |
|---|---|---|---|---|---|---|
| | 5° C. | | 10° C. | | 20° C. | |
| Treatments | 1993 | 1994 | 1993 | 1994 | 1993 | 1994 |
| *C. infirmo-miniatus* | NI | NI | 7.7a | 2.0a | 16.6b | 5.3a |
| *C. infirmo-miniatus* + TBZ | NI | NI | NI | NI | 3.3a | NI |
| *C. laurentii* | 6.6a | 3.3a | 21.5b | 7.8a | 19.9b | 10.8b |
| *C. laurentii* + TBZ | NI | NI | 3.3a | NI | 4.7a | NI |
| TBZ (15 ppm ai) | 5.7a | 7.8a | 12.3ab | 9.2a | 20.8b | 14.3c |
| TBZ (525 ppm ai) | NI | NI | NI | NI | 4.3a | NI |
| *P. expansum* | 36.2b | 36.2b | 33.7c | 29.7b | 34.3c | 30.0d |

NI, no visual infection at inoculated wound sites.
[y]The wounds were treated with a spore suspension of *P. expansum* (5.0 × 10³ ml⁻¹) alone, a mixture of TBZ (15 and 525 ppm ai) and *P. expansum*, or yeast suspension (2.0–3.0 × 10⁷ ml⁻¹) and *P. expansum* with a reduced rate of TBZ or without it. There were three replicates of 5 fruits each per treatment. Data were recorded after 35–40, 17–20, and 6–8 days of incubation at 5, 10 and 20° C., respectively.
[z]Within a column, values with the same letters are not significantly different at P = 0.05 according to Duncan's multiple range test.

Example 4

Control of Postharvest Brown Rot of Cherries Using Natural Saprophytic Yeast Colonists Fruits.

Sweet cherry fruits (cv. Lambert) were harvested on 15 Jun. 1994 at commercial maturity, stored at −1° C. and used within 20 days of harvest. Healthy-looking apple and cherry fruits were removed from cold storage for different experiments, surface sterilized with 0.105% sodium hypochlorite (The Clorox Co., Oakland, Calif.) for 2 minutes, rinsed with tap water, then air-dried. Cherry fruits were not wounded.

Biocontrol Yeasts.

The efficacy of *Cryptococcus infirmo-miniatus* strain YY6 and *C. laurentii* strain HRA5 alone or when integrated with a low dose of the fungicide iprodione (Rovral 50WP, 20 μg ai ml⁻¹) was tested for control of brown rot of sweet cherry using 2.0–3.0×10⁷ yeast cells per milliliter (6% transmittance at 550 nm).

Pathogens.

For *Monilinia fructicola*, diseased cherry fruits with extensive sporulation of the pathogen on their surface were collected from an orchard at the Mid-Columbia Agricultural Research and Extension Center. Spores of M. fructicola were removed by dipping 15 diseased fruits in 50 ml of SDWT, and the resulting suspension was sonicated for 3 minutes and vortexed for 1 minute. Spore concentrations were determined with a hemacytometer, and suspensions were used within 2–3 hours. The concentration of *Monilinia fructicola* used was $1.0 \times 10^4$ spores/ml.

Fruit Treatment.

Sweet cherry fruits were treated as described above with the following: *M. fructicola* alone, a mixture of iprodione (20 and 1175 µg ml$^{-1}$) and *M. fructicola*, or a yeast suspension and *M. fructicola* with the low rate of iprodione or without it. There were three replicates of 50 cherry fruits each. Fruits were transferred into nylon nets and immersed for one minute into treatment suspensions. Fruits were drained for two minutes and stored in perforated plastic bags at 2.8° C. Disease was evaluated after 20 days.

Statistical Analysis.

Disease incidence was the percentage of inoculated wounds that developed lesions. Percent data were subjected to arsine-square root transformation (Steel and Torrie, 1980) before analysis of variance, and means were separated by Duncan's multiple range test (P=0.05). Disease severity was the rot diameter of diseased wound sites and was statistically analyzed with the method above for incidence.

Results.

The reduction of brown rot of sweet cherry was not significant with *C. infirmo-miniatus*, *C. laurentii*, or the low rate of ipodione (Table 16). However, when either yeast was combined with the low rate of iprodione, significant (P=0.05) control was achieved, and the level of control was equivalent to that obtained with the full dose of iprodione.

Resistance of *M. fructicola* to iprodione has been reported (Elmer and Gaunt, Crop Protection 12:83–88, 1993). Because the mode of action of *C. infirmo-miniatus* and *C. laurentii* does not involve antibiosis, as discussed above, it is unlikely that resistance will develop to these yeasts.

Postharvest losses of sweet cherry to fungal decay occur despite application of fungicides and other recommended measures (Willett et al., Postharvest Pomology Newsl. 7:1–15, 1989). After the opening of the Japanese market in 1978 to U.S. cherries, the volume of exported cherries has steadily increased. At the same time, the need to reduce postharvest losses also has increased. Alternatives to fungicides are needed because Japan has not established a regulatory tolerance for postharvest fungicide residues (Dugan and Roberts, Phytopathol. 84:1031–1036, 1994). This is the first report of control of brown rot of sweet cherry with naturally-occurring saprophytic yeasts.

TABLE 16

Efficacy[y] of *Cryptococcus infirmo-miniatus* (strain YY6) and *Cryptococcus laurentii* (strain HRA5) alone or in the presence of a reduced rates (20 µg ml$^{-1}$) of iprodione in controlling disease incidence (%) of brown rot of sweet cherries (cv. Lambert) caused by *Monilinia fructicola*

| Treatments | Diseased Fruits (%)[z] |
| --- | --- |
| *C. infirmo-miniatus* | 14.7bc |
| *C. infirmo-miniatus* + iprodione | 2.0a |
| *C. laurentii* | 8.0abc |
| *C. laurentii* + iprodione | 0.7a |

TABLE 16-continued

Efficacy[y] of *Cryptococcus infirmo-miniatus* (strain YY6) and *Cryptococcus laurentii* (strain HRA5) alone or in the presence of a reduced rates (20 µg ml$^{-1}$) of iprodione in controlling disease incidence (%) of brown rot of sweet cherries (cv. Lambert) caused by *Monilinia fructicola*

| Treatments | Diseased Fruits (%)[z] |
| --- | --- |
| Iprodione (20 µg ml$^{-1}$) | 5.9abc |
| Iprodione (1175 µg ml$^{-1}$) | 1.3a |
| *Monilinia fructicola* | 17.5c |

[y]Healthy cherry fruits (cv. Lambert) were surface-sterilized, washed in running tap water and immersed in the suspension of *M. fructicola* ($1.0 \times 10^4$ per ml) alone, a mixture of iprodione (20 and 1175 µg ml$^{-1}$) and *M. frucucola*, or a yeast cell suspension ($4.0$–$6.0 \times 10^7$ per ml) and *M. fructicola* with a reduced rate (20 µg ml$^{-1}$) of iprodione or without it. There were three replicates of 50 fruits each per treatment. After treatments the fruits were allowed to drain for 2 min before storing them in perforated polythene bags. Treatments were randomized and placed in cardboard boxes lined with perforated polythene bags. Disease incidence was recorded after 20 days of incubation at 2.8° C.

[z]Within a column, values with the same letters are not significantly different at $P = 0.05$ according to Duncan's multiple range test.

Example 5

Population Studies of Yeasts in Pear Wounds

The ability of yeast cells to survive and multiply in wounds was studied to determine if these yeasts were effective colonizers of pear wounds. Fruits were wounded, inoculated with yeast cells, and held in plastic boxes at −1°, 5°, 10° and 20° C. Viable cell concentrations of the inoculum were determined by a modified dilution plate frequency technique (Chand et al., Appl. Environ. Microbiol. 58:3374–3379, 1992). Individual fruits served as one replicate in a randomized complete block design and three replicates were sampled at each sampling time and temperature. For the fruits incubated at 5°, 10° and 20° C., the wounds were sampled 0, 1, 2, 3, 4 and 7 days after inoculation, whereas at −1° C., the wound samples were removed 0, 3, 10, 15, 30 and 45 days after inoculation. Samples were taken using a cork borer (10 mm internal diameter) and macerated in distilled sterile water (Roberts, Phytopathol. 80:1051, 1990). Serial dilutions were plated in duplicate onto YMDA using the modified dilution plate frequency technique (Chand et al., Appl. Environ. Microbiol., 58:3374–3379, 1992) and incubated at 22°±2° C. for four days when yeast populations were counted and expressed as $\log_{10}$ CFU per wound.

Figure 2:
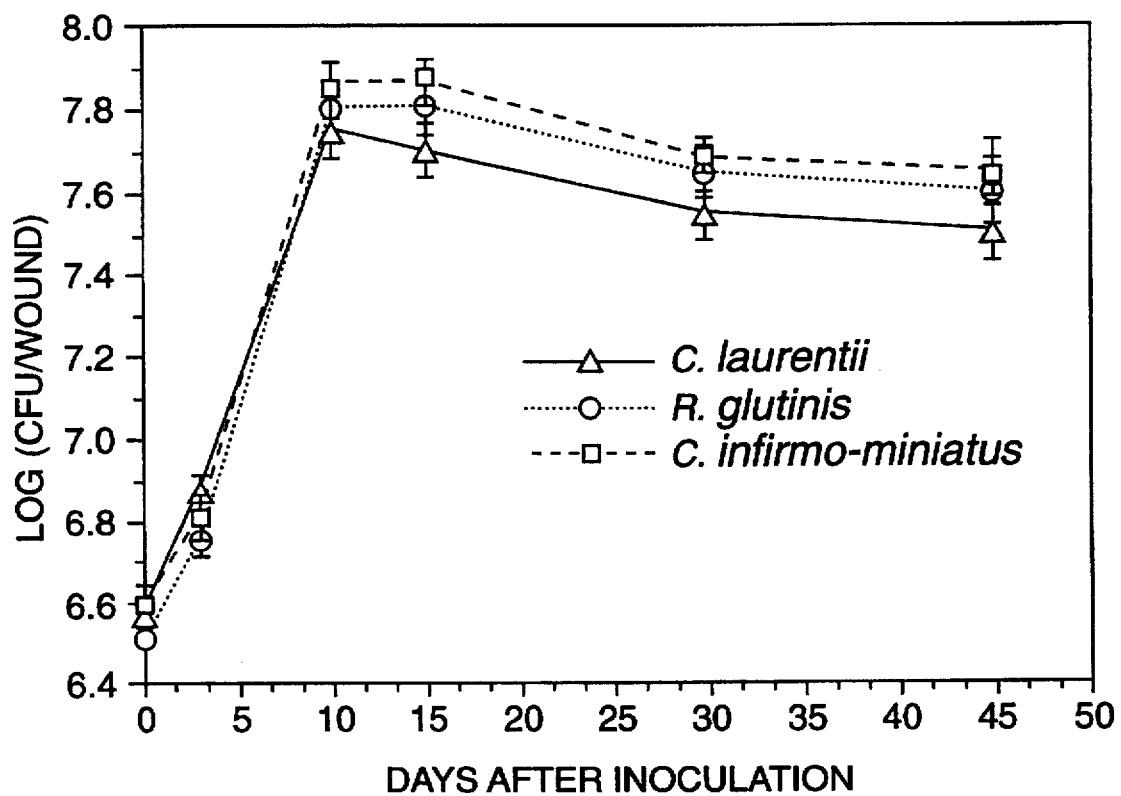
FIG. 2 shows the growth and population dynamics of *Cryptococcus laurentii, Rhodotorula glutinis*, and *Cryptococcus infirmo-miniatus* in wounds on pears stored at −1° C. Bars represent standard deviations of the means.
Figure 3A:
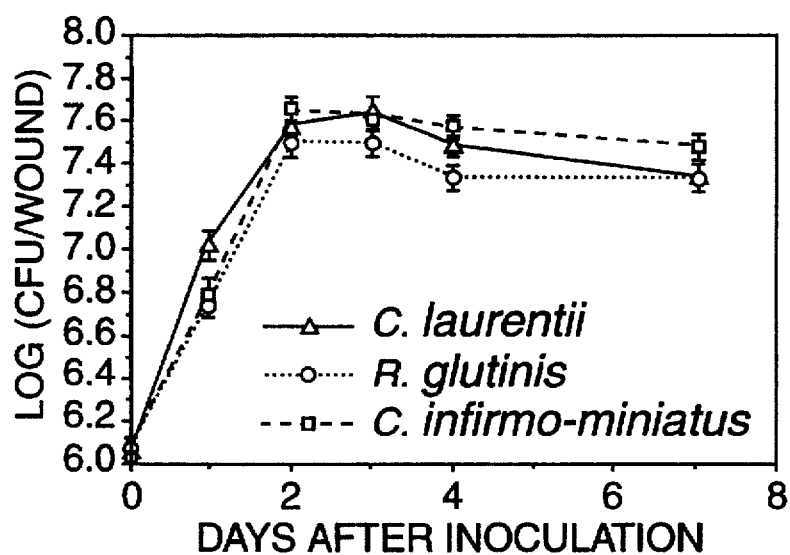
FIG. 3 shows the growth and population dynamics of *Cryptococcus laurentii, Rhodotorula glutinis*, and *Cryptococcus infirmo-miniatus* in wounds on pears stored at (A) 5° C., (B) 10° C., and (C) 20° C. Bars represent standard deviations of the means.
Figure 3B:
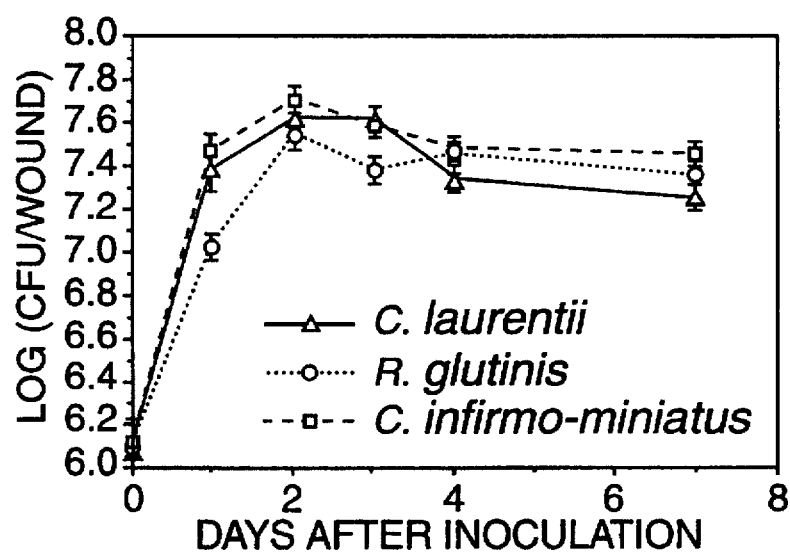
Figure 3C:
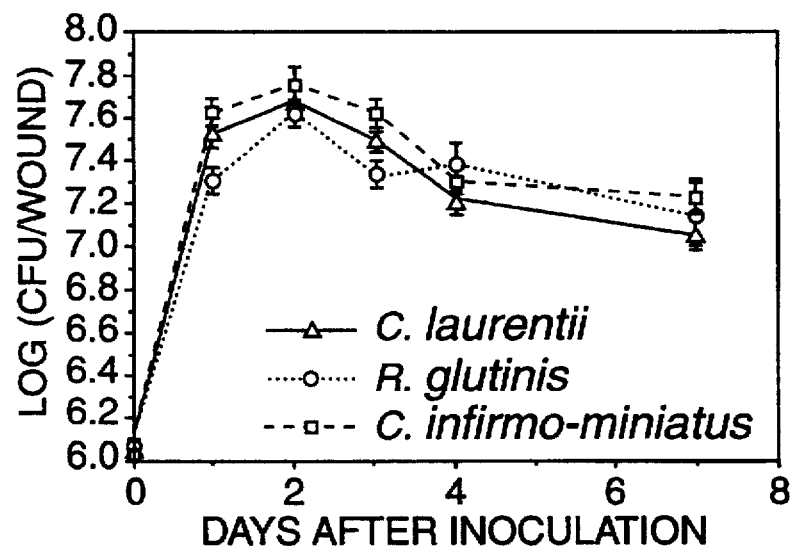

All yeasts colonized and multiplied in pear wounds at −1°, 5°, 10° or 20° C. (FIGS. 2 and 3). Yeast populations in wounds increased by approximately 1.3 log units over the initial populations within 10 days at −1° C. storage temperature, then started declining slowly (FIG. 2). After 45 days of storage, the population of yeasts in wounds was approximately 1.0 log unit higher than the population at the time of inoculation. At storage temperatures of 5°, 10° and 20° C., the maximum yeast populations, approximately 1.7 log units over the initial populations, were reached within two days of storage after inoculation (FIG. 3). After reaching the highest population in the wounds, there was faster decline as the storage temperature increased from 5° to 20° C.

Example 6

Mode of Antifungal Action of *C. laurentii*, *R. glutinis* and *C. infirmo-miniatus* Strains To determine if extracellular metabolites in culture broth were responsible for antagonism of *C. laurentii*, *R. glutinis* and *C. infirmo-miniatus* against *P. expansum*, yeasts were grown in YMDB at 22°±1° C. as described above. Yeast cells and culture broth were separated after two and seven days of incubation by centrifugation ($8.0 \times 10^3$ rpm $min^{-1}$). The supernatant was decanted then filter sterilized using a 0.2 μm polycarbonate membrane filter. Yeast pellets were washed twice with 50 ml of SDW (pH 6.8) and a cell suspension was made in SDW (1.5 to $2.0 \times 10^7$ $ml^{-1}$). A few microliters of concentrated spore suspension of *P. expansum* were added into the above supernatant and yeast cell suspensions so that the *P. expansum* spore concentration in the inoculation mixtures as $5.0 \times 10^3$ $ml^{-1}$. Fifty microliters of inoculation mixture was added into each puncture on surface sterilized, punctured fruits. There were three replications of five fruits per treatment. Treatments were randomized and incubated for 6 to 8 days at 20° C.

All wounds treated with *P. expansum* in water or yeast supernatants developed rots, indicating the absence of antifungal compounds in the culture of yeasts. Lesions that developed from wounds treated with a mixture of culture filtrate of the yeasts and *P. expansum* had 43±3 mm diameter whereas the average diameter of lesions treated with *P. expansum* in water was 33.5±3.5 mm. Wounds treated with double-washed cell suspensions of *C. laurentii*, *R. glutinis* and *C. infirmo-miniatus* reduced disease incidence to 45±5, 46±4, 50±6 percent, respectively, and the average diameter of diseased wounds was significantly smaller than controls.

To detect the production of antifungal metabolites by these yeasts, they were streaked on to YMDA in petri dishes, and plates were incubated at 22°±2° C. After 2, 4 and 7 days of incubation, a concentrated spore suspension of *P. expansum* (5.0 to $7.0 \times 10^7$ $ml^{-1}$) was atomized onto the plates. Plates were incubated at 22°±2° C. and observed daily for zones of inhibition for seven days.

Zones of inhibition did not develop around yeast growth on Petri plates, indicating that no antifungal compounds were produced by any of the three yeasts.

Because of their rapid growth rate at all temperature and lack of antifungal compounds, it is likely that fungal control was due to nutrient competition. However, induced resistance (i.e., the yeast or a yeast metabolite activates a resistance mechanism in the treated agricultural commodity), in vivo production of some enzymes (i.e., the yeast produces metabolites in wounds of the fruit that are not produced in culture or on an artificial medium), and hyperparasitism (the yeast directly parasitizes the pathogen by attacking spores and mycelia) may also play a role in control of postharvest diseases of pears by these saprophytic yeasts.

None of the three yeast strains used grew at 37° C., indicating that they cannot cause infection in the human body.

While this invention has been specifically described with reference to *Cryptococcus infirmo-miniatus spp.*, particularly Phaff and Fell isolate YY-6, *Cryptococcus albidus* isolate HRB-2, *Cryptococcus laurentii* (Kufferath) Skinner isolate HRA-5, *Rhodotorula aurantiaca* isolate YCL-5, and *Rhodotorula glutinis* Harrison isolates HRA-3, HRA-4, and HRB-6, it is to be understood that the invention is not so limited. Neither is the invention to be limited to the specific fungal pathogens described above.

All publications and published patent documents cited in this specification are incorporated herein by reference to the same extent as if each individual publication or patent application was specifically and individually indicated to be incorporated by reference.

Yeast strains useful in the practice of the present invention are available from the Mid-Columbia Agricultural Research and Extension Center, Hood River, Oreg. *Cryptococcus laurentii* strain HRA-5, *Rhodotorula glutinis* strain HRB-6, and *Cryptococcus infirmo-miniatus* strain YY-6 were deposited under the terms of the Budapest Treaty of Feb. 13, 1995, with the Agricultural Research Service Culture Collection (NRRL), Peoria, Ill. under accession numbers NRRL Y-21411, NRRL Y-21412, and NRRL Y-21413, respectively.

This invention has been detailed both by example and by direct description. It should be apparent that one having ordinary skill in this art would be able to surmise equivalents to the invention as described in the claims which follow but which would be within the spirit of the description above. Those equivalents are to be included within the scope of this invention.

What is claimed is:

1. A composition for biological control of a fungal disease of an agricultural commodity comprising an effective amount of a biologically pure yeast strain selected from the group consisting of *Cryptococcus infirmo-miniatus* Pfaff and Fell isolate YY-6, *Cryptococcus laurentii* (Kufferath) Skinner isolate HRA-5, *Rhodotorula glutinis* Harrison isolate HRB-6, and mixtures thereof.

2. A composition according to claim 1 further comprising a chemical fungicide.

3. A composition according to claim 2 wherein the chemical fungicide is a member of the group consisting of benomyl, carbendazim, thiabendazole, vinclozolin, iprodione, procymidon, dichlorfluanide, tebuconazole, prochloraz, fenethanil, diethefencarb, metomeclan, and chlorothalonil.

4. A composition according to claim 2 comprising a chemical fungicide in an amount about 25% or less of an amount that would be effective if the chemical fungicide were to be applied without the yeast strain, wherein the composition is more effective in reducing the incidence or severity of the fungal disease than a similar composition lacking the chemical fungicide.

5. A composition according to claim 4 comprising a chemical fungicide in an amount from 1.7% to 10% of an amount that would be effective if the chemical fungicide were to be applied without the yeast strain.

6. A composition according to claim 1 comprising an additional microbial biological control agent.

7. A composition according to claim 1 wherein the fungal disease is caused by a pathogen that is a member selected from the group consisting of *Pezicula malicorticis*, *Phialophora malorum*, and *Monilinea fructicola*.

8. A method for controlling a fungal disease of an agricultural commodity comprising applying to the agricultural commodity an effective amount of a composition comprising a biologically pure yeast strain selected from the group consisting of *Cryptococcus infirmo-miniatus* Pfaff and Fell isolate YY-6, *Cryptococcus laurentii* (Kufferath) Skinner isolate HRA-5, *Rhodotorula glutinis* Harrison isolate HRB-6, and mixtures thereof.

9. A method according to claim 8 wherein the fungal disease is caused by a pathogen selected from the group consisting of *Pezicula malicorticis*, *Phialophora malorum*, and *Monilinea fructicola*.

10. A method according to claim 7 further comprising applying to the agricultural commodity a composition comprising a chemical fungicide.

11. A method according to claim 10 wherein the chemical fungicide is selected from the group consisting of benomyl, carbendazim, thiabendazole, vinclozolin, iprodione, procymidon, dichlorfluanide, tebuconazole, prochloraz, fenethanil, diethefencarb, metomeclan, chlorothalonil, and mixtures thereof.

12. A method according to claim 10 wherein the chemical fungicide is applied in an amount about 25% or less of an amount that would be effective if the chemical fungicide were to be applied without the yeast strain, wherein the method is more effective in reducing the incidence or severity of the fungal disease than if the chemical fungicide is not applied.

13. A method according to claim 12 wherein the chemical fungicide is applied in an amount from 1.7% to 10% of an amount that would be effective if the chemical fungicide were to be applied without the yeast strain.

14. A composition comprising a biologically pure strain of *Cryptococcus or Rhodotorula* that (a) increases in number by at least one log within ten days at 0° C. in apple wounds or at −1° C. in pear wounds and (b) is effective in reducing by at least 50% the incidence or severity of a fungal disease of an agricultural commodity caused by a fungus selected from the group consisting of *Phialophora malorum, Pezicula malicorticis*, and *Monilinea fructicola*, wherein the strain is selected from the group consisting of *Cryptococcus infirmo-miniatus* Pfaff and Fell isolate YY-6, *Cryptococcus laurentii* (Kufferath) Skinner isolate HRA-5, *Rhodotorula glutinis* Harrison isolate HRB-6, and mixtures thereof.

15. A composition of claim 14 wherein the fungus is *Pezicula malicorticis*.

16. A composition of claim 14 wherein the strain is a strain of Cryptococcus.

17. A composition of claim 16 wherein the yeast strain is a strain of *Cryptococcus infirmo-miniatis*.

18. A composition of claim 14 wherein the strain is a strain of *Cryptococcus infirmo-miniatis* or *Cryptococcus laurentii*.

19. A composition of claim 14 wherein the yeast strain is a strain of Rhodotorula.

20. A composition of claim 19 wherein the yeast strain is a strain of *Rhodotorula glutinis*.

21. A composition comprising (a) a biologically pure strain of Cryptococcus or Rhodotorula that increases in number by at least one log within ten days at 0° C. in apple wounds or at −1° C. in pear wounds and is effective in reducing by at least about 50% the incidence or severity of a fungal disease of an agricultural commodity and (b) a chemical fungicide in an amount about 25% or less of an amount that would be effective if the chemical fungicide were to be applied without the yeast strain, wherein the composition is more effective in reducing the incidence or severity of the fungal disease than a similar composition lacking the chemical fungicide, wherein the strain is selected from the group consisting of *Cryptococcus infirmo-miniatus* Pfaff and Fell isolate YY-6, *Cryptococcus laurentii* (Kufferath) Skinner isolate HRA-5, *Rhodotorula glutinis* Harrison isolate HRB-6, and mixtures thereof.

22. A composition of claim 21 comprising a chemical fungicide in an amount from 1.7% to 10% of an amount that would be effective if the chemical fungicide were to be applied without the yeast strain.

23. The composition of claim 21 that is effective in reducing by at least about 50% the incidence or severity of a fungal disease of an agricultural commodity caused by a fungus selected from the group consisting of *Phialophora malorum, Pezicula malicorticis*, and *Monilinea fructicola*.

* * * * *